US006344475B1

(12) United States Patent
Caplan et al.

(10) Patent No.: US 6,344,475 B1
(45) Date of Patent: Feb. 5, 2002

(54) CONDUCTANCE OF IMPROPERLY FOLDED PROTEINS THROUGH THE SECRETORY PATHWAY

(75) Inventors: Michael J. Caplan, Woodbridge; Marie E. Egan, Branford, both of CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/427,696

(22) Filed: Oct. 27, 1999

Related U.S. Application Data

(60) Provisional application No. 60/105,806, filed on Oct. 27, 1998.

(51) Int. Cl.[7] .................. A61K 31/38; A61K 31/47; A61K 47/00
(52) U.S. Cl. .................. 514/431; 514/311; 514/772; 514/851
(58) Field of Search ................ 514/431, 311, 514/772, 851

(56) References Cited

U.S. PATENT DOCUMENTS

| | | | |
|---|---|---|---|
| 4,866,072 A | 9/1989 | Edwards et al. | 514/291 |
| 5,384,128 A | 1/1995 | Meezan et al. | 424/450 |
| 5,674,898 A | 10/1997 | Cheng et al. | 514/557 |
| 5,886,026 A | 3/1999 | Hunter et al. | 514/449 |
| 6,015,828 A | 1/2000 | Cuppoletti | 514/397 |

FOREIGN PATENT DOCUMENTS

| | | | |
|---|---|---|---|
| WO | WO 93/13768 | | 7/1993 |
| WO | WO 95/05810 | | 3/1995 |
| WO | 98/23294 | * | 6/1998 |
| WO | WO 98/37878 | | 9/1998 |

OTHER PUBLICATIONS

Pasch et al., The effect of halothane, enflurane and isoflurance on resistance and compliance in patients with asthma or chronic obstructive lung disease, Anaesthesist, (Feb. 1991) 40(2) pgs 65–71.*
Bargon et al., 1992. Down–Regulation of Cystic Fibrosis Transmembrane Conductance Regulator Gene Expression by Agents That Modulate Intracellular Divalent Cations. *Molecular and Cellular Biology*. 12(4): 1872–1878.
Boucher, 1992. Drug Therapy in the 1990s. What Can We Expect for Cystic Fibrosis? *Drugs*. 43(4): 431–439.
Treiman et al., 1998. A Tool Coming of Age: Thapsigargin as an Inhibitor of Sarco–Endoplasmic Reticulum $Ca^{2+}$–ATPases. *Tips*. 19:131–135.
Wagner et al., 1995. Molecular Strategies for Therapy of Cystic Fibrosis. *Annu. Rev. Pharmacol. Toxicol.* 35: 257–76.
Yang et al., 1993. The Common Variant of Cystic Fibrosis Transmembrane Conductance Regulator Is Recognized by hsp70 and Degraded in a Pre–Golgi Nonlysosomal Compartment. *Proc. Natl. Acad. Sci. USA*. 90: 9480–9484.
Amara et al., *Trends Cell. Biol.* 2:145–149.
Chao et al., *J. Clin. Invest.* 96(4):1794–1801 (1995).
Cheng et al., *Cell* 63:827–834 (1990).
Choudhury et al. *J. Biol. Chem.* 272(20):13446–13451 (1997).
Clark et al. (*J. Orthop. Res.* 12(5):601–611 (1994).
Gregory et al., *Nature* 347:382–386 (1990).
Hobbs et al., *Ann Rev Genetics* 24:133–170 (1990).
Hughes et al., *PNAS* 94:1896–1901 (1997).
Kinoshita et al., *Ann Rev Med* 47, 1–10 (1996).
Lau et al., *J Biol Chem* 264:21376–21380 (1989).
Le et al., *J. Biol. Chem.* 269:7514–7519.
Lytton et al., *J. Biol. Chem.* 266:17067–17071 (1991).
Nauseef, *J. Lab. Clin. Med.* 134(3);215–221 (1999).
Fuchs et al., *New England Journal of Medicine* 331:637–642 (1994).
Parker et al., *EMBO J.* 14(7):1294–1303 (1995).
Pind et al., *J. Biol. Chem.* 269:12784–12788.
Pogador et al., *PNAS* 94:13140–13145 (1997).
Rich et al., *Nature* 347:358–363 (1990).
Rouard et al., *J.Biol. Chem.* 274(26):18487–18491 (1999).
Sheppard et al. *Physiol. Rev.* 79:Suppl: S23–S34 (1999).
Sousa et al., *Cellular and Molecular Biology* 42: 609–616 (1996).
Stein et al., *Nat. Struct. Biol.* 2:96–113 (1995).
Thomas et al., *J. Biol. Chem.* 267:5727–5730 (1992).
Travis et al., *Annu. Rev. Biochem.* 52:655–709 (1983).
Ward et al., *Cell* 82: 121–127 (1995).
Yu et al., *Nature Structural Biology* 2:363–367 (1995).

* cited by examiner

*Primary Examiner*—Kevin E. Weddington
(74) *Attorney, Agent, or Firm*—Choate, Hale & Stewart; Brenda Herschbach Jarrell; Monica R. Gerber

(57) ABSTRACT

This invention provides the methodology and agents for treating any disease or clinical condition which is at least partly the result of endoplasmic reticulum-associated retention of proteins. Thus, the methods and agents of the present invention provide for the release of normally retained proteins from the endoplasmic reticulum. The present invention is particuarly useful for treating any disease or clinical condition which is at least partly the result of endoplasmic reticulum-associated retention or degradation of mis-assembled or mis-folded proteins.

48 Claims, 5 Drawing Sheets

FIG. IA
Excised at −50mV
- - -> 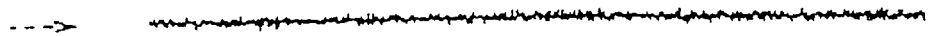
2 minutes after excision, 1mM ATP in the bath, −80mV
- - -> 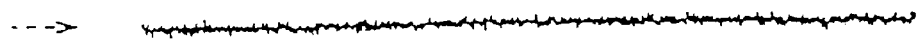
2 minutes later, +80mV
- - -> 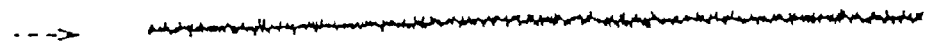
FIG. IB
Excised at −50mV
- - -> 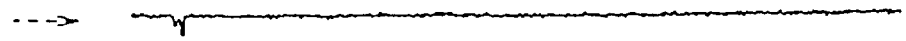
2 minutes after excision, 1mM ATP in the bath, −80mV
- - -> 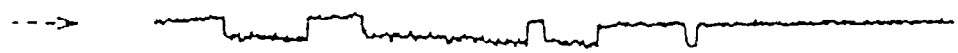
2 minutes later, +80mV
- - -> 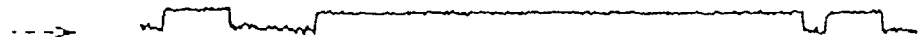

CONDUCTANCE OF IMPROPERLY FOLDED PROTEINS THROUGH THE SECRETORY PATHWAY

This Application claims benefit to Provisional Application No. 60/105,806 filed Oct. 27, 1998.

ACKNOWLEDGMENT OF FEDERAL SUPPORT

The present invention arose in part from research funded by the following NIH grants: GM-42136 and DK-17433.

FIELD OF THE INVENTION

This invention provides the methodology and agents for treating any disease or clinical condition which is at least partly the result of endoplasmic reticulum-associated retention of proteins. Thus, the methods and agents of the present invention provide for the release of normally retained proteins from the endoplasmic reticulum. The present invention is particularly useful for treating any disease or clinical condition which is at least partly the result of endoplasmic reticulum-associated retention or degradation of mis-assembled or mis-folded proteins.

BACKGROUND

All publications and patent applications herein are incorporated by reference to the same extent as if each individual publication or patent application was specifically and individually indicated to be incorporated by reference.

A. Introduction

Protein folding and quality control machinery has been implicated in the molecular pathogenesis of several human diseases caused by defective intracellular transport of an aberrantly folded protein through the secretory pathway. Exemplary diseases include pulmonary emphysema resulting from severe plasma α-antitrypsin deficiency and cystic fibrosis resulting from mutations in the cystic fibrosis transmembrane conductance regulator (Amara et al., *Trends Cell. Biol.* 2:145–149; Le et al., *J. Biol. Chem.* 269:7514–7519; Pind et al., *J. Biol. Chem.* 269:12784–12788). This invention is directed to the treatment and cure of such diseases.

Although the treatment and cure of cystic fibrosis and Chronic Obstructive Pulmonary Disease have been chosen as representative diseases for the purpose of describing and explaining the present invention, the compositions and/or methods of the present invention are applicable to the treatment and cure of any disease which involves the defective intracellular transport of mis-folded proteins.

B. Cystic Fibrosis—An Overview of the Diseases, Protein and Gene

The Disease of Cystic Fibrosis

Cystic Fibrosis (CF) is an inherited multi-system metabolic disorder of the eccrine and exocrine gland function, usually developing during early childhood and affecting mainly the pancreas, respiratory system and sweat glands. Glands which are affected by CF produce abnormally viscous mucus, usually resulting in chronic respiratory infections, impaired pancreatic and digestive function, and abnormally concentrated sweat. CF is also called Clarke-Hadfield syndrome, fibrocystic disease of the pancreas and mucoviscidosis.

CF is the most common fatal autosomal recessive disease in Caucasians affecting approximately 1 in 2000 or 2500 live births, with 1 person in 25 being a heterozygote (Boat et al., *Metabolic Basis of Inherited Disease* 2649–2680 (McGraw-Hill, 1989)). It is a complex disorder mainly affecting the ability of epithelial cells in the airways, sweat glands, pancreas and other organs and tissues to secrete chloride ions (Cl−), leading to a severe reduction of the accompanying sodium and water in the mucus. Thus, the primary defect in CF is the relative impermeability of the epithelial cell to chloride ions (Cl−). This defect results in the accumulation of excessively thick, dehydrated and tenacious mucus in the airways, with subsequent bacterial infections, mucus blockage and inflammation. For a detailed discussion of the clinical manifestations, diagnosis, complications and treatment of the disease, see R. C. Bone, *Cystic Fibrosis*, In J. C. Bennett et al., *Cecil Textbook of Medicine* 419–422 (W. B. Saunders Co., 1996).

The CF Protein and Gene

The gene for CF is located on the long arm of chromosome 7. For a description of the gene, the expression of the gene as a functional protein, and confirmation that mutations of the gene are responsible for CF, see Gregory et al., *Nature* 347:382–386 (1990); Rich et al., *Nature* 347:358–363 (1990); and Watson et al., *Recombinant DNA*, pp. 525–529 (Scientific American Books, 1992).

The protein encoded by the CF-associated gene is the cystic fibrosis transmembrane conductance regulator (CFTR). CFTR is a cyclic AMP-dependent chloride channel found in the plasma membrane of certain epithelial cells. CFTR contains approximately 1480 amino acids and is made up of two repeated elements, each comprising six transmembrane segments and a nucleotide binding domain. The two repeats are separated by a large, polar, so-called R-domain containing multiple potential phosphorylation sites. Based on its predicted domain structure, CFTR is a member of a class of related proteins which includes the multi-drug resistance or P-glycoprotein, bovine adenyl cyclase, the yeast STE6 protein as well as several bacterial amino acid transport proteins (Riordan et al., *Science* 245:1066–1073 (1989); Hyde et al., *Nature* 346:362–365 (1990)). Proteins in this group are characteristically involved in pumping molecules into or out of cells.

Gene Mutations Responsible for CF

The metabolic basis for CF results from a mutational defect in a specific chloride channel. Naturally-occurring, single amino acid mutations have been found in the first nucleotide binding fold of CFTR. Although over 800 different mutations have been identified in the CF associated gene, the most common is a deletion of three nucleotides which results in the loss of a phenylalanine residue at position 508 of CFTR (ΔF508) (Davis et al., *Am. J. Respir. Crit. Care Med.* 154:1229–1256 (1996); Sheppard and Welsh, *Physiol. Rev.* 79:Suppl: S23–S45 (1999)).

Additional examples of CFTR mutants include G551D, a mutation in the CFTR gene resulting in a substitution of aspartic acid for glycine at amino acid 551 of the CFTR (U.S. Pat. No. 5,602,110), and several naturally-occurring CFTR mutants carrying a defect in the first nucleotide binding fold (NFB1) (U.S. Pat. No. 5,434,086).

Mutations at position 508 contribute to approximately 90% of all CF cases, although the percentage varies by race and geographical location (Kerem et al., *Science* 245:1073–1080 (1989)). This mutation results in the failure of an epithelial cell chloride channel to respond to cAMP (Frizzel et al., *Science* 233:558–560 (1986); Welsh, *Science* 232:1648–1650 (1986); Li et al., *Science* 244:1353–1356 (1989); Quinton, *Clin. Chem.* 35:726–730 (1989)). Although CF-affected epithelial cells are unable to normally up-regulate apical membrane Cl− secretion in response to agents which increase cAMP, they do increase Cl− secretion in response to increases in intracellular $Ca^{2+}$.

There are at least three different chloride channels found in epithelial cells, including volume sensitive, calcium-dependent and cAMP-dependent. In normal individuals, chloride channels are located on the luminal membranes of epithelial cells. When these channels are open, chloride ions move into the airway lumen, producing an osmotic gradient that draws water into the lumen. In cystic fibrosis the absence or dysfunction of at least one of these chloride channels, CFTR, results in the failure to secrete chloride in response to cAMP stimulation therefore there is an inadequate amount of water on the luminal side of the epithelial membranes as well as excessive sodium reabsorption. In airway cells this causes abnormal mucus secretion with inadequate water content, ultimately leading to pulmonary infection and epithelial damage. Abnormal electrolytes in the sweat of CF patients probably results from the impermeability of the sweat duct epithelium to chloride. In airway cells this causes abnormal mucus secretion with inadequate water content, ultimately leading to pulmonary infection and epithelial cell damage.

Physiologically, the ($\Delta$F508) mutant CFTR is mis-folded and unable to assume its appropriate tertiary conformation (Thomas et al., *J. Biol. Chem.* 267:5727–5730 (1992)), and is retained in the endoplasmic reticulum (ER) as a result of the mutation-induced mis-folding and eventually targeted for degradation (Cheng el al., *Cell* 63:827–834 (1990); Ward et al., *Cell* 83:122–127 (1995)). Other examples of processing mutants leading to CFTR chloride channel dysfunction, with the frequency of the mutation in parentheses, include: D1507 (0.5), S549I (very rare), S549R (0.3), A559T (very rare) and N1303K (1.8) (Welsh e al., *Cell* 73:1251–1254 (1993)). P574H and A455E are additional CF-associated mutants which are also mis-processed (Ostedgaard el al., *J. Cell. Sci.* 112(Pt13):2091–2098 (1999)). Only 5% to 10% of the mis-folded CFTR protein of these two mutants reaches the apical membrane.

Because more than 98% of CF patients die from either respiratory failure or pulmonary complications before reaching maximum physiological maturity, the therapeutic goals have historically been to prevent and treat the complications of obstruction and infection in the airways, enhance mucous clearance, and improve nutrition. The identification of the $\Delta$F508 defect (and other mutations in CFTR) has facilitated the rapid development of proposed treatments for CF, including the therapeutic introduction of the wild-type CFTR gene via gene therapy, as well as more traditional drug therapies.

Treatment of Cystic Fibrosis Using Traditional Drugs

Traditional treatments for CF include chest physiotherapy (e.g., percussion and postural drainage), various bronchodilators, nutritional supplements (e.g., pancreatic enzymes and vitamins), exercise and rehabilitation, and long-term oxygen therapy for chronic hypoxemia. Aerosolized amiloride has been administered to improve the quality of the secretions, thereby improving the air flow in CF patients (U.S. Pat. Nos. 4,501,729 and 4,866,072). Although these methods have increased the overall survival and physical comfort of CF patients, the traditional drugs and treatment methodologies do not cure the afflicted individuals and CF-afflicted persons often [times] are not expected to live beyond their mid-twenties or early thirties. (R. C. Bone, supra).

DNase Treatment

One identified new drug treatment for CF has been the use of DNase, such as human DNase 1, which ameliorates one of the side effects caused by the defect in CFTR (*New England Journal of Medicine* 331:637–642 (1994)). Although the water content of bronchial secretions is probably the critical determinant of secretion viscosity, it is believed that DNA from lysed cells may add to this index.

Increased Permeability of Epithelial Cells to $Cl^-$

U.S. Pat. No. 5,384,128 discloses a method of treating CF which comprises administration of an epithelial cell chloride permeability enhancing composition which is a nontoxic, nonionic surfactant having (1) a critical micelle concentration of less than about 10 mM and a hydrophile-lipophile balance number of from about 10 to 20, and (2) a suitable hydrophobic organic group joined by a linkage to a suitable hydrophobic polyol. Examples of such compositions include a saccharide joined with organic groupings, such as an alkyl, aryl, aralkyl, or fatty acid group; polyoxyethylenes joined with an organic grouping; or, alkyl polyoxyethylene sorbitans. The preferred method of treatment is by aerosol inhalation.

Treatment of Cystic Fibrosis Using Gene Therapy

Several methods of gene therapy have been developed and are being tested for providing the normal CFTR gene into CF patients. For example, transfecting the normal CFTR gene into the nasal epithelial cells of patients has been shown to improve functions of the transmembrane chloride channel. These results have raised the hope that delivery of retroviral vectors containing normal CFTR genes directly to the lung epithelium by means of aerosol will help alleviate CF. Despite promising results, implementation of gene therapy methodologies to "cure" CF still remain in the experimental stages. As a result, an efficacious drug alternative to proposed gene therapy treatments is needed to more effectively treat CF.

D. Chronic Obstructive Pulmonary Disease: An Overview of the Disease, Protein and Gene The Disease The designation Chronic Obstructive Pulmonary Disease (COPD) is an imperfect, although widely used, term because it includes several specific disorders with different clinical manifestations, pathologic findings, therapy requirements, and prognoses. The term encompasses chronic bronchitis and emphysema. Common to most of these diseases is chronic involvement of peripheral (small) airways or, more rarely, localized obstruction of central (large) airways. For a comprehensive overview of COPD, see Matthay et al., *Chronic Airways Diseases*, In *Cecil Textbook of Medicine* (Bennet el al., eds.; W. B. Saunders Company) 20th Ed., 52:381–309 (1996)).

Since elastase released by activated neutrophils is rendered inactive by the inhibitor $\alpha$-antitrypsin (AAT), diminished circulating levels of AAT can result in proteolytic destruction of lung elastin, a phenomenon implicated in the pathogenesis of COPD (Travis et al., *Annu. Rev. Biochem.* 52:655–709 (1983); Beith, *Front. Matrix Biol.* 6:1–4 (1978)).

The $\alpha$-Antitrypsin (AAT) Protein and Gene

Human AAT is a 394-amino acid protein glycosylated at three specific asparagine residues (Carrell et al., In *Proteinase Inhibitors* (Barrett et al., eds.; Elsevier, Amsterdam) 403–420 (1986); Long et al, *Biochemistry* 23:4828–4837 (1984); Yoshida et al., *Arch. Biochem. Biophys.* 195:591–595 (1979)). AAT is a member of the serine proteinase inhibitor superfamily (Huber et al., *Biochemistry* 28:8951–8966 (1989)). It is folded into a highly ordered tertiary structure containing three $\beta$-sheets, nine $\alpha$ helices, and three internal salt bridges (Loebermann et al., *J. Mol. Bio.* 177:531–556 (1984)).

Gene Mutations Responsible for COPD

The human AAT structural gene is highly polymorphic and several alleles exhibit a distinct mutation predicted to preclude conformational maturation of the encoded polypeptide following biosynthesis (Brantly et al., *Am. J*

Med. 84:13–31 (1988); Stein et al., *Nat. Struct. Biol.* 2:96–113 (1995)). Genetic variants of human AAT unable to fold into the native structural conformation are poorly secreted from hepatocytes (Laurell et al., *In Protease Inhibitors in Plasma* (Putnam, ed.; Academic Press, New York) Vol. 1:229–264 (1975); Peters et al., In *Plasma Protein Secretion by the Liver* (Glaumann et al., eds.; Academic Press, New York) 1–5 (1983); Sifers et al., *Semin. Liver Dis.* 12:301–312 (1992); Sifers et al., In *The Liver: Biology and Pathology* (Arias et al., eds.; Raven Press Ltd., New York) 3rd Ed. 1357–1365 (1994)).

Choudhury et al. (*J. Biol. Chem.* 272(20):13446–13451 (1997)) report on a secretion-incompetent variant null of α-antitrypsin designated as Hong Kong.

E. Overview of the Invention

The current invention is based on the unexpected discovery that inhibition of UGGT or other elements of the ER-chaperon retention machinery allows mis-folded or mis-assembled proteins, such as mis-folded mutant (ΔF508) CFTR protein and mutant α-antitrypsin (Hong Kong), to exit the ER instead of being targeted for degradation. By preventing the normal action of UGGT or other elements of the ER-chaperon retention machinery, the mis-folded proteins exit the ER and are targeted to the plasma membrane, where despite the mutation, they can function. This invention has practical applications in treating or curing any disorder or disease which directly or indirectly results from mis-folded ER proteins including, but not limited to, clinical conditions related to the misfolding and/or non-release of the transmembrane precursors of the glycosylphosphatidylinositol-linked proteins, low density lipoprotein receptor, the thyroid prohormone thyroglobulin (Tg), Class I histocompatibility proteins as occurs in tumors and in numerous viral infections, as well as CFTR and α-antitrypsin.

While many groups are currently trying to overcome these types of diseases and clinical conditions through gene therapy, the approach of the present invention employs chemical pharmaceuticals to rescue the endogenous mutant protein. It is likely, therefore that our method will not be limited by the current challenges which confront gene therapy efforts, including low multiplicity of transformation, low levels of expression, and inflammation and immune responses to the requisite viral vectors. Recent deaths associated with experimental gene therapies further indicate the need for alternative treatment methods. Our approach is also the first to attempt to defeat ER retention of mis-folded proteins by interfering directly with ER quality control mechanisms.

As described in detail herein, this invention encompasses various compositions and methods which reduce the activity of UGGT and thereby permit exiting of mis-folded and mis-assembled proteins from the ER. Such compositions include compounds which covalently bond to modified UGGT and irreversibly inhibit its catalytic function. Exposure to oligonucleotides whose sequences are antisense to the UGGT coding sequence will also reduce UGGT expression and activity. Optimal UGGT activity requires high concentrations of $Ca^{2+}$. Our research also demonstrates that interfering with UGGT activity by depleting ER $Ca^{2+}$ stores through various treatments, such as with calcium pump inhibitors, allows the mis-folded but functional ΔF508 CFTR protein to "escape" from the ER and reach the cell surface. Thus, our discovery also provides novel and clinically applicable treatment for reversing or preventing diseases or clinical conditions which result from the ER-associated retention or degradation of mis-assembled or mis-folded glycoproteins.

SUMMARY OF THE INVENTION

This invention provides methods of treating any disease or clinical condition by administering an agent that permits the release of proteins from the ER. More particularly, this invention provides such methods wherein the disease or clinical condition is at least partly the result of endoplasmic reticulum-associated retention or degradation of mis-assembled or mis-folded proteins.

In one embodiment of the invention, methods are provided wherein the agent permits release of mis-assembled or mis-folded proteins from the endoplasmic reticulum.

In another embodiment of the invention, methods are provided wherein the proteins being released are glycoproteins.

The methods of the present invention are useful for treating diseases or clinical conditions such as Cystic Fibrosis, Chronic Obstructive Pulmonary Disease, Paroxysmal Nocturnal Hemoglobinuria, Familial Hypercholesterolemia, Tay-Sachs Disease, viral diseases, neoplastic diseases, Hereditary Myeloperoxidase Deficiency or Congenital Insulin Resistance.

In one embodiment of the invention, the methods involve using agents which act as calcium pump inhibitors.

In another embodiment of the invention, the methods involve using agents which decrease or inhibit the functional activity of UDP glucose:glycoprotein glycosyl transferase.

In still another embodiment of the invention, the methods involve using agents which decrease or inhibit activity of the endoplasmic reticulum $Ca^{++}$ ATPase.

In yet another embodiment of the invention, the methods involve using agents which lower the concentration of $Ca^{++}$ in the endoplasmic reticulum.

In another embodiment of the invention, the methods involve using agents which cause release of $Ca^{++}$ from the endoplasmic reticulum.

In yet another embodiment of the invention, the methods involve using agents which decrease or inhibit $IP_3$ receptor activity.

In still another embodiment of the invention, the methods involve using agents which decrease or inhibit calnexin functional activity.

Examples of agents which are useful in the methods of the present invention include, but are not limited to, thapsigargin or a derivative thereof, cyclopiazonic acid or a derivative thereof, DBHQ or a derivative thereof, or halothane or a derivative thereof.

Additional examples of agents which are useful in the methods of the present invention include, but are not limited to, oligonucleotides which are antisense to UDP glucose:glycoprotein glycosyl transferase, calnexin or $Ca^{++}$ ATPase.

The present invention also provides methods wherein the agents are administered to the pulmonary system, such as by using an aerosol.

The present invention provides methods of releasing a mis-assembled or mis-folded glycoprotein from the endoplasmic reticulum of a cell by administering an agent that decreases or inhibits the functional activity of UDP glucose:glycoprotein glycosyl transferase.

The present invention also provides methods of releasing a mis-assembled or mis-folded glycoprotein from the endoplasmic reticulum of a cell by administering an agent that decreases or inhibits activity of the endoplasmic reticulum $Ca^{++}$ ATPase.

The present invention also provides methods of releasing a mis-assembled or mis-folded glycoprotein from the endoplasmic reticulum of a cell by administering an agent that lowers the concentration of $Ca^{++}$ in the endoplasmic reticulum.

The present invention also provides methods of releasing a mis-assembled or mis-folded glycoprotein from the endoplasmic reticulum of a cell by administering an agent that decreases or inhibits calnexin functional activity.

The present invention also provides methods of increasing the permeability of the apical surfaces of airway epithelial cells to a chloride ion by administering an agent that decreases or inhibits the intracellular retention of mis-assembled or mis-folded glycoproteins.

The present invention further provides methods of increasing the permeability of the apical surfaces of airway epithelial cells to a chloride ion by administering an agent that decreases or inhibits the activity of UDP glucose:glycoprotein glycosyl transferase.

The present invention also provides methods of increasing the permeability of the apical surfaces of airway epithelial cells to a chloride ion by administering an agent that decreases or inhibits activity of the endoplasmic reticulum $Ca^{++}$ ATPase.

The present invention further provides methods of increasing the permeability of the apical surfaces of airway epithelial cells to a chloride ion by administering an agent that lowers the concentration of $Ca^{++}$ in the endoplasmic reticulum.

The present invention also provides methods of increasing the permeability of the apical surfaces of airway epithelial cells to a chloride ion by administering an agent that decreases or inhibits calnexin functional activity.

The present invention further provides methods of treating cystic fibrosis or alleviating the symptoms of cystic fibrosis by administering an agent that decreases or inhibits the activity of UDP glucose:glycoprotein glycosyl transferase.

The present invention also provides methods of treating cystic fibrosis or alleviating the symptoms of cystic fibrosis by administering an agent that decreases or inhibits activity of the endoplasmic reticulum $Ca^{++}$ ATPase.

The present invention further provides methods of treating cystic fibrosis or alleviating the symptoms of cystic fibrosis by administering an agent that lowers the concentration of $Ca^{++}$ in the endoplasmic reticulum.

The present invention further provides methods of treating cystic fibrosis or alleviating the symptoms of cystic fibrosis by administering an agent that decreases or inhibits calnexin functional activity.

The present invention provides methods of screening candidate compounds to identify an agent that inhibits endoplasmic reticulum-associated retention or degradation of a mis-assembled or mis-folded glycoprotein, wherein the method includes the steps of:

a). treating a cell exhibiting intracellular retention of a mis-assembled or mis-folded glycoprotein in the endoplasmic reticulum with the candidate compound; and b). determining whether the mis-assembled or mis-folded glycoprotein is released from the endoplasmic reticulum, thereby identifying the candidate compound as an agent that causes the release of a malformed mis-folded glycoprotein from the endoplasmic reticulum.

The present invention also provides methods of screening candidate compounds to identify an agent that inhibits the functional activity of UDP glucose:glycoprotein glycosyl transferase, wherein the method includes the steps of:

a). treating a cell exhibiting intracellular retention of a mis-assembled or mis-folded glycoprotein in the endoplasmic reticulum with the candidate compound; and b). determining whether the mis-assembled or mis-folded glycoprotein is released from the endoplasmic reticulum, thereby identifying the candidate compound as an agent that causes the release of a mis-assembled or mis-folded glycoprotein from the endoplasmic reticulum.

The present invention provides aerosol formulations of thapsigargin, DBHQ or cyclopiazonic acid.

In addition, the present invention provides compositions which include two or more of the following agents: 1) an agent that decreases or inhibits the activity of UDP glucose:glycoprotein glycosyl transferase, 2) an agent that decreases or inhibits activity of the endoplasmic reticulum $Ca^{++}$ ATPase, 3) an agent that decreases or inhibits $IP_3$ receptor activity, and 4) an agent that decreases or inhibits calnexin functional activity.

DESCRIPTION OF THE FIGURES

FIG. 1. CFTR chloride channel activity in excised patches from CF-affected airway epithelial cells in control conditions or after treatment with thapsigargin. Cells were pre-treated with IBMX (100 $\mu$M) and forskolin (10 $\mu$M) prior to patch excision. Initially patches were held at –50 mV, and then stepped through a voltage protocol from ±10 mV to ±90 mV. 1 mM ATP was present in the bath to prevent channel rundown.

A. Representative single channel current traces from a membrane patch excised from untreated IB3-1 cells. No low conductance chloride channel activity was seen. Arrows indicate closed state.

B. Representative single channel currents from a membrane patch excised from an IB3-1 cell after treatment with thapsigargin. Low conductance chloride channel activity can be seen as the downward deflections in the current traces. Arrows indicate closed state.

Figure 2A:
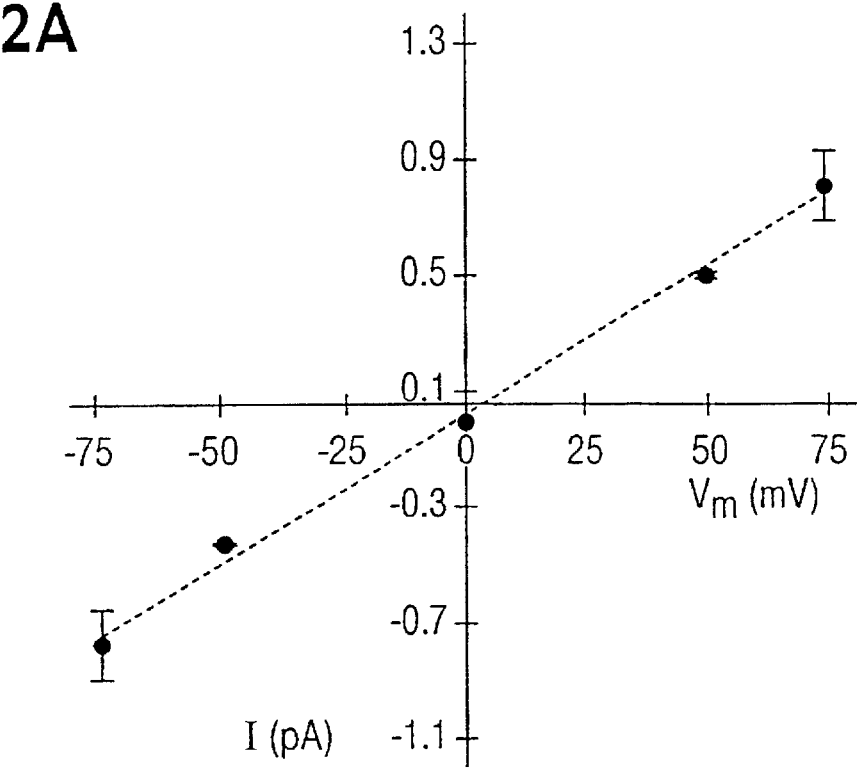
Figure 2B:
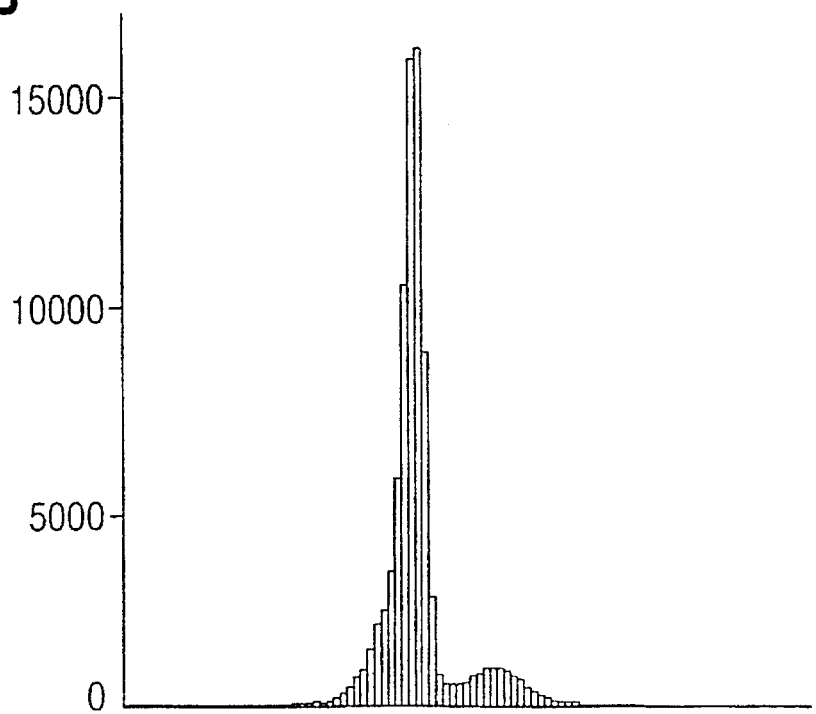

FIG. 2. Characteristics of CFTR channels in CF-affected airway epithelial cells after thapsigargin treatment.

A. The current versus voltage relationship of the low conductance channels depicted in FIG. 1B is plotted. The average single channel conductance was 11.8 pS.

B. All points histogram at ±80 mV. The area under the first peak represents time spent in the closed state, while the area under the second peak represents time spent in the open state. The calculated open state probability is 0.12.

Figure 3:
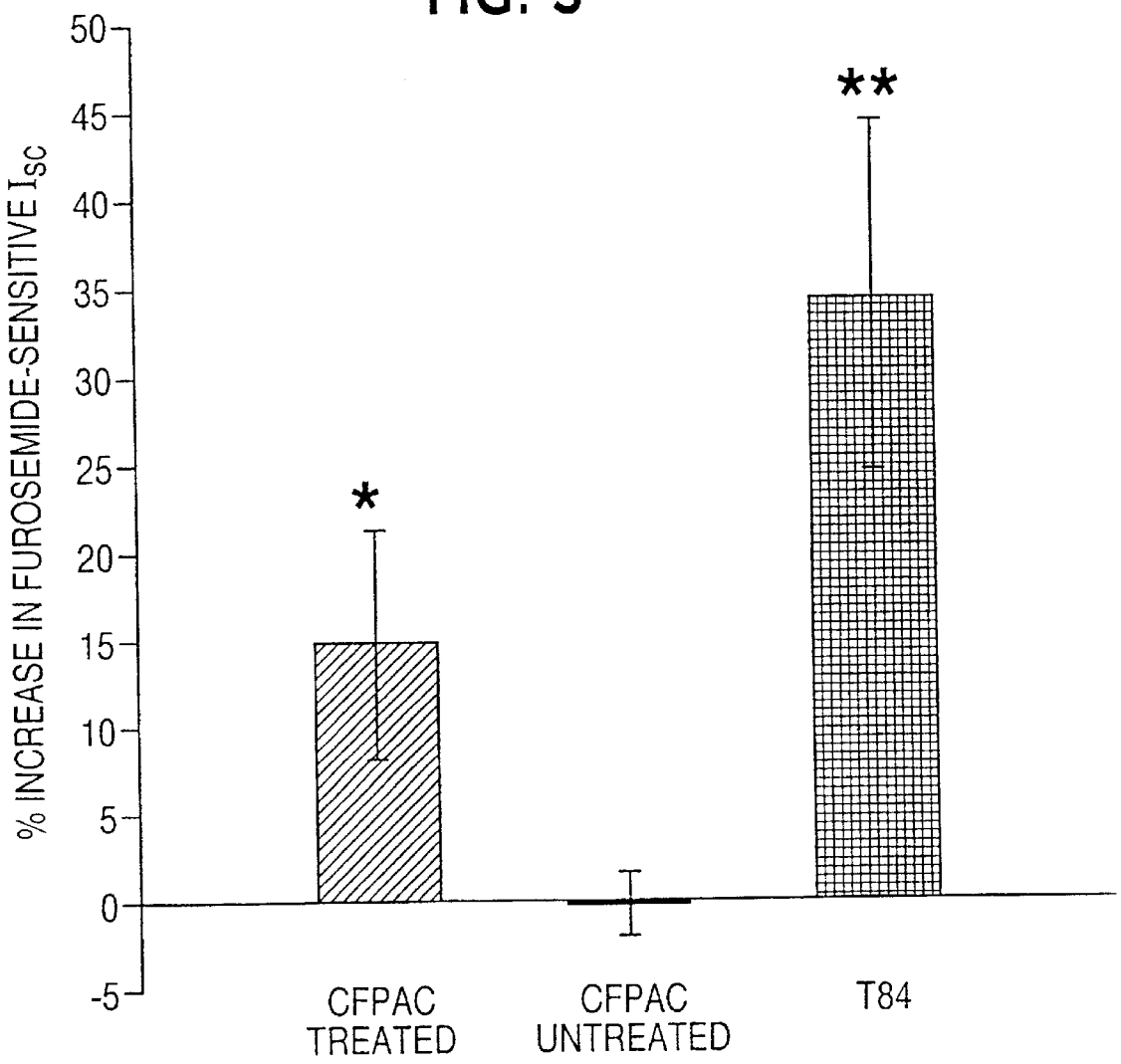

FIG. 3. The effects of elevation of cytosolic cAMP on short circuit current. Monolayers of CFPAC or T84 cells were exposed to a cAMP-stimulation cocktail of 10 $\mu$M forskolin and 100 $\mu$M IBMX. The bars indicate the % increase in $I_{SC}$ that is furosemide sensitive detected after treatment with the cAMP stimulation cocktail. The asterisks mark a significant difference between untreated CFPAC cells (n=12) and either the thapsigargin treated CFPAC cells (p=0.02, *) (n=12) or the T84 cells (p=0.004, **) (n=12). Error Bars=SEM.

Figures 4A, 4B, 4C, 4D:
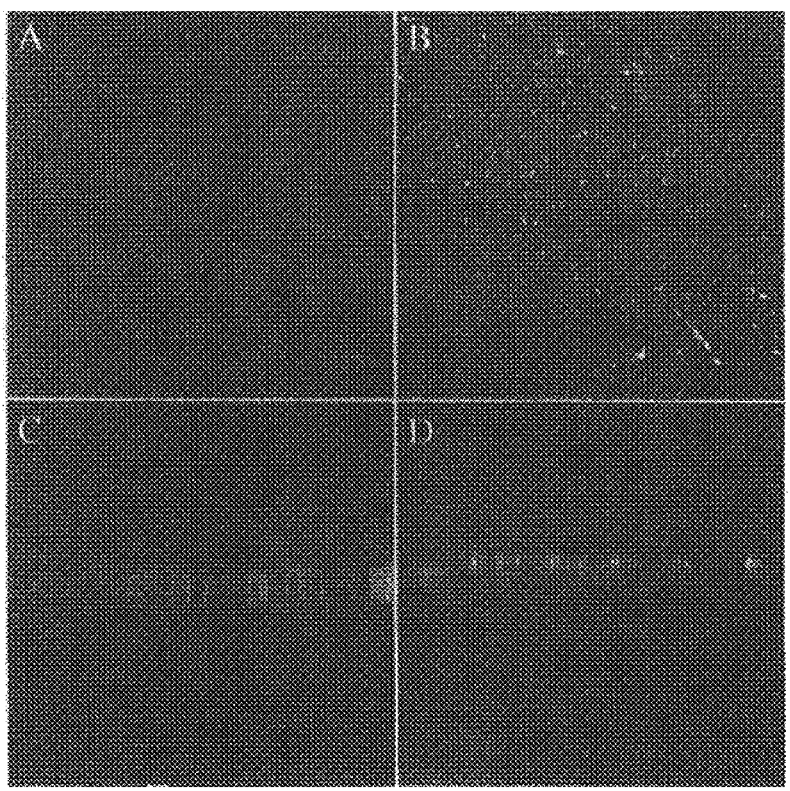

FIG. 4. Confocal immunofluorescent localization of the mutant ΔF508 CFTR protein in untreated and thapsigargin-treated CF-PAC cells. Untreated CF-PAC cells or CF-PAC cells which had been treated with thapsigargin were subjected to confocal immunofluorescence labeling using an antibody directed against the CFTR protein.

When viewed en face (A) or in XZ cross-section (C), the untreated cells revealed a staining pattern consistent with an exclusively intracellular localization of the CFTR protein. No cell surface labeling could be detected. In contrast, thapsigargin-treated cells viewed en face (B) or in XZ cross-section (D) reveal bright staining of microvilli at the apical plasma membrane. The intracellular signal is markedly diminished in the treated cells. Thus, thapsigargin treatment induces the relocalization of the ΔF508 mutant CFTR protein from an intracellular compartment to its site of appropriate functional residence at the apical cell surface. The width of the monolayer is 11μ.

Figures 5A, 5B, 5C, 5D, 5E, 5F:
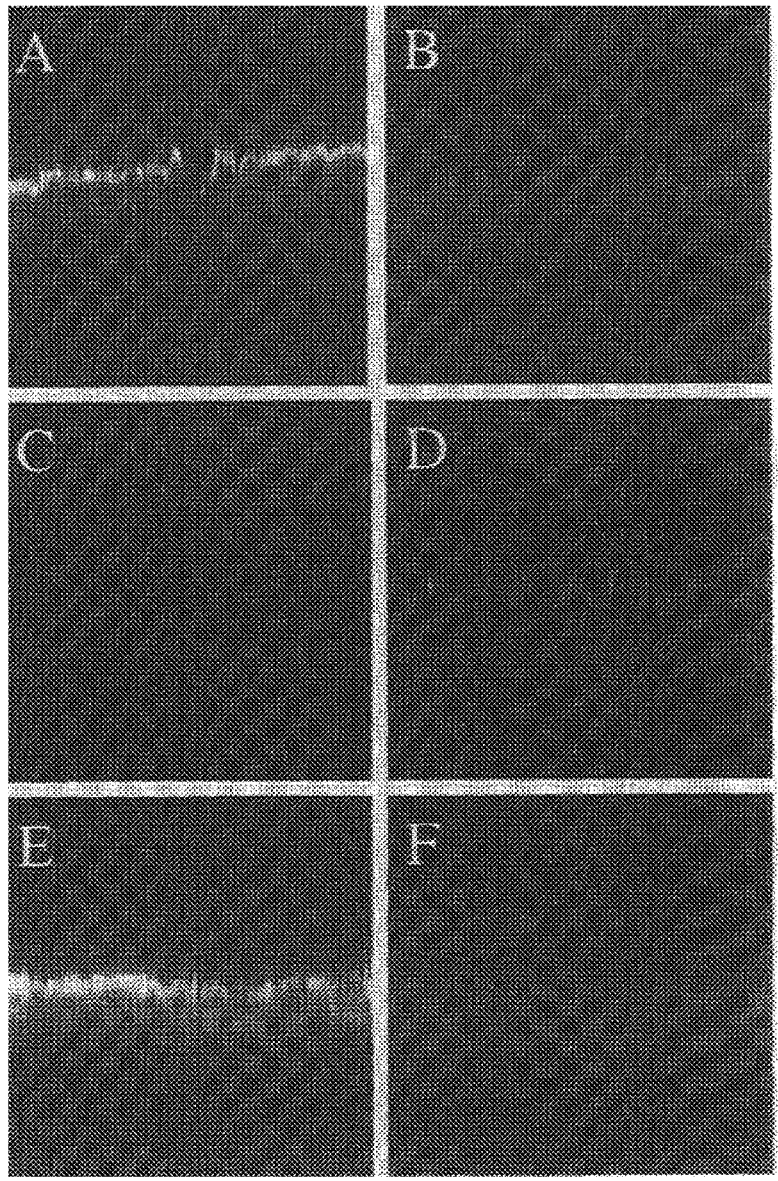

FIG. 5. Distribution of the ΔF508 CFTR protein in ΣCFBE290− CF airway epithelial cells exposed to nebulized thapsigargin. ΣCFBE290− airway epithelial cells were grown to confluence on permeable filter supports. Cells were exposed to thapsigargin dissolved in the media bathing their apical surfaces (A,B), to nebulized thapsigargin (E,F) or were not thapsigargin-treated (C,D) and processed for immunofluorescence. Panels A, C and E depict the immunofluorescent staining of the ΔF508 CFTR protein; panels B, D and F depict the basolateral localization of the Na,K-ATPase α-subunit. The ΔF508 CFTR protein can not be detected in untreated cells, but is present to the same extent at the apical surfaces of cells treated with nebulized or dissolved thapsigargin. The width of the monolayer is 9μ.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

A. Definitions

Antisense

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

Clinical Condition

Any symptom or disorder related to any disease.

Combinatorial Chemistry

"Combinatorial chemistry," as used herein, refers to the numerous technologies used to create hundreds or thousands of chemical compounds, wherein each of the chemical compounds differ for one or more features, such as their shape, charge, and/or hydrophobic characteristics.

Disease

A pathological condition of a cell, body part, an organ, a tissue, or a system resulting from various causes, wherein such causes include, but are not limited to, infections, genetic defects or environmental stresses.

Mis-assembled

As used herein, "mis-assembled" refers to hetero- or homo-oligomeric proteins that have not or can not attain their appropriate or functionally mature quaternary structure.

Mis-folded

As used herein, "mis-folded" refers to proteins that have not or can not attain their appropriate or functionally mature tertiary structure.

Nebulized

As used herein, "nebulized" refers to converting a liquid to a fine spray. A medicated spray is one form of the nebulization of a liquid.

Nucleic Acid Sequence

"Nucleic acid sequence," as used herein, refers to an oligonucleotide, nucleotide, or polynucleotide, and fragments or portions thereof, and to DNA or RNA of genomic or synthetic origin which may be single- or double-stranded, and represents the sense or antisense strand. Similarly, "amino acid sequence" as used herein refers to an oligopeptide, peptide, polypeptide, or protein sequence, and fragments or portions thereof, and to naturally occurring or synthetic molecules.

UGGT

As used herein, "UGGT" refers to UDP-Glc:glycoprotein glycosyl transferase, also known as UDP glycoprotein glycosyl transferase and as UDP-glucose:glycoprotein glucosyl transferase. UGGT is an ER enzyme that attaches glucose to malformed/improperly folded glycoproteins, but not to native glycoproteins.

B. Elevation of Cyclic AMP Levels

As discussed above, CFTR is a cAMP-dependent chloride channel. Cyclic AMP is composed of adenosine monophosphate with the phosphate group bonded internally to form a cyclic molecule. Cyclic AMP (cAMP) is generated from adenosine triphosphate (ATP) by the enzyme adenylcyclase and is active in the regulation of gene expression of both prokaryotes and eukaryotes.

Administration of compositions which increase or supplement the cAMP levels of epithelial cells has been used in an attempt to activate Cl⁻ conductance to near wild type levels (U.S. Pat. No. 5,434,086). A preferred compound for increasing cAMP levels is a phosphodiesterase inhibitor, such as methylxanthine phosphodiesterase inhibitor. Phosphodiesterase inhibitors increase cAMP levels by inhibiting cAMP breakdown. Other examples of phosphodiesterase inhibitors include nonspecific inhibitors such as alkylxanthines and cAMP-specific inhibitors such as Rolipram (Shearing AG). Preferred alkylxanthines include the methylxanthines, such as 3-isobutyl-1-methylxanthine (IBMX) and 1,3-dimethylxanthine (theophylline) and other xanthines such as papaverine, pentoxifilline and caffeine. For a review of phosphodiesterase inhibitors, see Nicholson et al., *Trends Pharmacol. Sciences* 12:19 (1991) and Beavo et al., *Trends Pharmacol. Sciences* 11:150 (1990).

Treating ΔF508-C127 cells and human ΔF508 airway epithelial cells with a carboxylic acid or a carboxylate, such as butyrate (e.g., sodium butyrate), resulted in the generation of cAMP-dependent chloride channel activity (U.S. Pat. No. 5,674,898).

Supplemental cAMP and analogs thereof or beta adrenergic receptor agonists, such as isoproterenol and albuterol, can also be used to increase cAMP levels.

Guanosine monophosphate (GMP) becomes a cyclic molecule by a phosphodiester bond between the 3' and 5' atoms. Cyclic GMP (cGMP) acts at the cellular level as a regulator of various metabolic processes, possibly as an antagonist to cAMP.

Combination therapy which includes administration of an inhibitor specific for a cGMP-inhibited type III cAMP phosphodiesterase, an adenylate cyclase activator, and a cAMP or a cAMP analog has also been proposed for treating CF (U.S. Pat. No. 5,602,110). Inhibitors which are specific for a cGMP-inhibited type III cAMP phosphodiesterase include amrinone, milrinone, anagrelide, cilostamide and fenoxamine. Adenylate cyclase activators include forskolin, cholera toxin and beta-adrenergic receptor agonists.

C. Calcium-ATPase Inhibitors

Correct distribution of $Ca^{+2}$ ions within the cellular compartments is required for their well-established function as molecular signals in eukaryotic cells (Cheek, T. R., *Curr. Opin. Cell. Biol.* 3:199–205 (1991); Pietrobon et al., *Eur. J. Biochem.* 193:599–622 (1990)). ATP-dependent $Ca^{+2}$ uptake from the cytosol to ER lumen is a prerequisite for rapid cytosolic signaling through receptor-mediated $Ca^{+2}$ release (Berridge, M. J., *Nature* 361:315–325 (1993)).

The ATP-requiring $Ca^{+2}$ transport to the ER lumen is accomplished by a family of ER $Ca^{+2}$ ATPases termed SERCA ATPases. $Ca^{+2}$-ATPase inhibitors may be therapeutically useful in treating CF by improving $Cl^-$ secretion in epithelial cells. Proposed $Ca^{+2}$-ATPase inhibitors for use in the present invention, include, but are not limited to, thapsigargin, cyclopiazonic acid (CPA) and 2,5-di-(tert-butyl)-1,4-hydroquinone (DBHQ) (A. C. Chao et al., *J. Clin. Invest.* 96(4):1794–1801 (1995) and U.S. Pat. No. 5,384,128). Thapsigargin is described in more detail below. CPA is an indole derivative isolated from liquid cultures of *Penicillium cyclopium*, *Aspergillis flavus* and *Aspergillis versicolor* (Luk et al., *Applied and Environmental Microbiology* 211–212 (1977)). DBHQ is a commercially available non-toxic synthetic compound chemically unrelated to either thapsigargin or CPA.

Using the CF-derived pancreatic epithelial line CFPAC-1, Chao et al., supra, found that DBHQ stimulated $^{125}I$ efflux and mobilized intracellular free $Ca^{+2}$ in a dose-dependent manner. Pretreatment of monolayers of CFPAC-1 cells with DBHQ for 4–5 minutes significantly increased the $Ca^{+2}$-independent or autonomous activity of $Ca^{+2}$/calmodulin-dependent protein kinase (CaMKII) assayed in cell homogenates.

D. Opening the ER $Ca^{+2}$ Channels

Activators which lower ER $Ca^{+2}$ by a different mechanism than thapsigargin are also encompassed by this invention.

1D-myo-inositol 1,3,4-(or 1,4,5-)triphosphate ($IP_3$), a hydrophilic inositol phosphate, induces the intracellular release of $Ca^{+2}$ stores from the ER through its specific interactions with the $IP_3$ receptor (e.g., a calcium channel protein containing an $IP_3$ binding site). Thus, the present invention also encompasses agents that open ER $Ca^{+2}$ channels by acting as $IP_3$ receptor agonists. An inhibitor of $IP_3$ receptor activity is heparin (U.S. Pat. Nos. 5,886,026 and 5,171,217).

A determination of $IP_3$ concentration in cell extracts can be carried out by means of a sensitive competitive binding test using an $IP_3$ binding protein, $H^3$-labeled $IP_3$ and unlabeled $IP_3$ (U.S. Pat. No. 5,942,493). An assay kit for this purpose is available from Amersham (TRK 1000) and the determination can be carried out as described in the assay protocol.

E. Temperature-Dependent Delivery of the Mutant CFTR to the Plasma Membrane

Experiments with 3T3 fibroblast cells and C127 cells grown at lower temperatures for a period of time have shown a shift in the glycosylation pattern of ΔF508 CFTR towards a more mature CFTR protein. Normal CFTR protein appears to be unaffected by the lower temperature. It has been hypothesized that at reduced temperatures there is an increased flux of the mutant protein through the Golgi complex. Thus, it has been suggested that exposing a patient's lung epithelia to a temperature below normal body temperature for a period of time might mobilize mutant CFTR to the plasma membrane of the lung epithelial cells, where the mutant CFTR can mediate chloride transport (U.S. Pat. No. 5,674,898). One hypothetical method involves implanting in the patient's lung a non-toxic, non-immunogenic agent which lowers the temperature in the vicinity of the lung so that it is below normal body temperature.

F. Purinergic Receptors and $Cl^-$ Secretion

Purinergic receptors play an important role in regulating $Cl^-$ secretion in epithelial cells. Inoue et al. (*Am. J. Physiol. Cell Physiol.* 272(6):41–46 (1997)) assayed the human intestinal epithelial cell line, Caco-2, for $Cl^-$ secretion by measuring the short-circuit current. The researchers found that responses to purinergic receptor agonists were inhibited by pretreatment with 1,2-bis(2-aminophenoxy)ethane-N,N,N',N'-tetraacetic acid-acetoxymethyl ester, thapsigargin or quinine.

G. CF and UDP-Glucose:Glycoprotein Glycosyl Transferase

As discussed above, the primary lesion in cystic fibrosis is associated with mutations in the gene encoding the CFTR which prevent it from functioning as a chloride channel at the apical surfaces of airway epithelial cells. The most common mutation (ΔF508), which occurs in 67.2% of cystic fibrosis patients, results in the synthesis of a CFTR protein which is unable to fold correctly and assume its appropriate tertiary conformation. Consequently, the protein is retained in the ER by the ER's "quality control" machinery. Several other CFTR mutations also result in mis-folding and ER retention.

Both nascent α-antitrypsin and nascent CFTR form transient associations with calnexin (also designated as p88 or IP90), a calcium-binding protein of the ER membrane. Since calnexin functions as a molecular chaperone for glycoproteins and interacts with monoglucosylated oligosaccharides, reglucosylation may function to initiate assembly between unfolded glycoproteins and the molecular chaperone (Hammond et al., *Proc. Natl. Acad. Sci. U.S.A.* 91:913–917 (1994)).

The UGGT Protein and Gene

UGGT was found to have an apparent monomeric $M_r$ of 150 kDa following isolation and purification from rat liver microsomes (Trombetta et al., *J. Biol. Chem.* 267:9236–9240 (1992)). The soluble, 170 kDa UGGT isolated from Drosophila has an amino acid sequence of 1548 amino acids beginning with a signal peptide and terminating in a potential ER retrieval signal, HGEL (C. G. Parker et al., *EMBO J.* 14(7):1294–1303 (1995)). The amino acid sequence was found to lack any putative transmembrane domains. The gene coding for UGGT, designated as gpt1, has also been identified in *Schizosaccharomyces pombe* (Fernandez el al., *EMBO J.* 15(4):705–13 (1996)). This gene codes for a polypeptide having a signal peptide of 18 amino acids followed by 1429 amino acids with no transmembrane domain and a C-terminal tetrapeptide designated PDEL.

Functional Role of UGGT

UGGT adds glucose from UDP-glucose to high mannose glycoproteins in the presence of $Ca^{2+}$ ions and the resulting glucosylated oligosaccharide has the same structure as the processed intermediate, $Glc_1Man_9GlcNAc_2$ (Trombetta et al., *Biochemistry* 28:8108–8116 (1989)). Unfolded, denatured glycoproteins are substantially better substrates for glycosylation by the enzyme than are the corresponding native proteins.

Proteins that fail to fold properly are retained in the ER (or in a ER-Golgi intermediate compartment), where they are proteolytically degraded. UGGT is proposed to be involved in the quality control of glycoprotein folding in the ER (Parker et al., supra; Fernandez et al., supra; M. C. Sousa and A. J. Parodi, The interaction of UDP-Glc:Glycoprotein Glucosyl transferase with the acceptor glycoprotein, *Cellular and Molecular Biology* 42:609–616 (1996); Sousa M C and Parodi A J., The molecular basis for the recognition of mis-folded glycoproteins by the UDP-Glc:Glycoprotein Glucosyl transferase, *EMBO J* 14:4196–4203 (1995)). UGGT participates together with lectin-like chaperones that recognize monoglucosylated oligosaccharides in the control mechanism by which cells only allow passage of properly folded glycoproteins to the Golgi apparatus (Labriola et al., *J. Cell Biol.* 130(4):771–9 (1995)).

Cycles of transient interaction with UGGT, each resulting in reglucosylation of attached oligosaccharides, is believed to facilitate interaction between unfolded glycoproteins and calnexin and ensure the intracellular retention of improperly folded glycoproteins in the ER. Calnexin binds to glucose residues which are exposed on the N-linked sugar chains of membrane proteins.

We have developed a novel strategy that releases mis-folded ΔF508 CFTR protein from the ER and allows it to be functionally expressed at the cell surface. Treatment of CF airway epithelial cells with thapsigargin, which reduces the calcium concentration in the ER lumen, leads to functional expression of the ΔF508 protein at the cell surface as revealed by electrophysiologic and immunofluorescence analysis. The dose of thapsigargin employed in these studies appears to be tolerable and induces an effect whose magnitude is probably sufficient to produce clinically significant improvements in airway epithelial function in cystic fibrosis patients.

It has been shown that UGGT requires millimolar calcium concentrations for optimal activity (Trombetta and Parodi, 1992). In cells expressing wild type α1 antitrypsin, treatment with thapsigargin retards or prevents the secretion of the protein (Kuznetsov et al., 1993; Lodish and Kong, 1990). This is apparently due to stable association of the newly synthesized α1-antitrypsin with UGGT in the endoplasmic reticulum when calcium levels in the ER are reduced (Choudhury et al., 1997). It has also been shown that lowering ER calcium through application of thapsigargin or calcium ionophores retards the exit of numerous wild type proteins from the ER and increases their rate of degradation (Wilkstrom and Lodish, 1993; Sudbeck et al., 1997; van Weering et al. 1998; Clark et al., 1994; Wong et al., 1993; Wileman et al., 1991; Lodish et al., 1992; Lodish and Kong, 1990). Apparently, if the UGGT enzyme is denied calcium, it binds tightly to its substrates (i.e. newly synthesized glycoproteins) but is unable to release them, perhaps because successful completion of the glucose transfer step is required to effect release.

It is interesting to speculate as to why, in the case of α1-antitrypsin, thapsigargin retards protein exit from the ER, whereas in the case of ΔF508 CFTR exit from the ER is stimulated by this drug (see Examples 1–6). We propose that in cells expressing a mutant protein that is incapable of proper folding, mis-folded protein is present in the ER in quantities which constitute a large molar excess over the resident quantity of UGGT. Under normal circumstances, the mis-folded protein binds to UGGT, undergoes addition of a glucose residue and is rapidly released (Hammond and Helenius, 1995). The glucosylated protein is retained in the ER via interactions with calnexin, and a sufficient pool of UGGT is available to interact with mis-folded proteins that have lost their glucose tag. When ER calcium is depleted, each molecule of UGGT becomes stably complexed with a mis-folded protein, and thus unavailable to interact with the remaining mis-folded proteins in the ER. Since the mis-folded proteins are present in large molar excess over the UGGT, the excess mis-folded protein is free to escape the UGGT-mediated quality control system and to exit the ER. In contrast, in cells that do not express a mutant mis-folded protein, we hypothesize that UGGT exists in large molar excess over its potential substrates. Thus, when ER calcium is depleted, UGGT acts as a sink that can bind up newly synthesized proteins that have not completed their folding. Consequently, the bulk of newly synthesized proteins are retained in the ER.

Finally, it must be noted that the mechanism through which calcium pump inhibitors effect the release of ΔF508 CFTR from the ER may not be related directly to the calcium requirements of ER chaperone machinery. It is possible, for example, that depletion of calcium from the ER lumen is sufficient to facilitate the spontaneous folding of the ΔF508 CFTR protein, permitting it to acquire a stable conformation and bypass chaperone retention. In either case, it is clear that calcium pump inhibition is sufficient to release a cohort of ER-retained ΔF508 CFTR to the cell surface, where it can function appropriately (see Examples 1–6).

H. Applications for Non-CF Protein Release

In addition to CF, a large and growing list of disease states is associated with protein retention in the ER (Amara J, Cheng S and Smith A., Trends in Cell Biol 2:145–149 (1992); Bychkova V and Ptitsyn O, Folding intermediates are involved in genetic diseases?, *FEBS Lett* 359:6–8 (1995)). Several are listed and briefly discussed below.

α1-antitrypsin Deficiency

The α1-antitrypsin protein is synthesized in the liver and secreted into the circulation. It serves to prevent damage to the lungs induced by inflammatory processes. Absence of this protein leads to pulmonary scarring and emphysema. In the most common forms of human α1-antitrypsin deficiency, a mutation leads to the synthesis of an α1-antitrypsin molecule which can not fold properly and is consequently not secreted but rather is retained in the liver cell ER (Yu M, Lee K and Kim J, The Z type variation of human alpha 1-antitrypsin causes a protein folding defect, *Nature Structural Biology* 2:363–367 (1995)).

Paroxysmal Nocturnal Hemoglobinuria

In red blood cells, the inventory of glycosylphosphatidylinositol (GPI) linked proteins includes a pair of polypeptides, Decay Accelerating Factor (DAF) and CD59, which help to protect the erythrocytes from being accidentally injured by complement-mediated cell lysis. One of the proteins which participates in the synthesis of the GPI anchor is a sugar transferase encoded by the PIG-A gene (phospatidylinositol glycan-class A). This gene is located on the X chromosome. In Paroxysmal Nocturnal Hemoglobinuria, a spontaneous mutation occurs in the PIG-A gene in just one of the many precursor cells which give rise to erythrocytes (Kinoshita et al., Role of Phosphatidylinositol-Linked Proteins in Paroxysmal Nocturnal Hemoglobinuria Pathogenesis, *Ann Rev Med* 47, 1–10 (1996)). All of the erythrocytes which arise from this particular precursor, therefore, are deficient in GPI-linked protein synthesis. The transmembrane precursors of the GPI-linked proteins are retained in the ER and degraded. Consequently, these cells lack DAF and CD59 expression and are susceptible to complement attack and lysis. Patients with Paroxysmal Nocturnal Hemoglobinuria are likely to become anemic and can suffer life threatening disorders of clotting and bone marrow function. A treatment which liberated the transmembrane precursors of GPI-linked proteins from the ER and allowed them to travel to the cell surface might prevent or ameliorate the symptoms of this disease.

Familial Hypercholesterolemia

The disease known as Familial Hypercholesterolemia (FHC) is caused by a defect in the gene encoding the low density lipoprotein (LDL) receptor which results in the synthesis of receptors that can not internalize LDL from the cell surface (Goldstein et al., Receptor-Mediated Endocytosis: Concepts Emerging from the LDL Receptor System, *Ann. Rev. Cell Biol.* 1, 1–39 (1985)). In the absence of functional LDL receptors, cells are unable to import exogenous cholesterol. Even though serum cholesterol levels rise to extraordinarily high levels, cells are unaware of its presence since they lack the machinery that allows them to endocytose LDL. The excess cholesterol synthesis results in the build up of cholesterol-filled lipid droplets in cells throughout the body. Accumulation of these cholesterol inclusions in the smooth muscle cells that populate arterial walls produces atherosclerotic plaques, which can go on to occupy and occlude the lumens of the blood vessels themselves. A subset of the mutations in the gene encoding the LDL receptor which lead to FHC in humans (the class II mutations) lead to the synthesis of LDL receptors which can not fold properly and which are retained in the ER (Yamamoto et al., Deletion in cysteine-rich region of LDL receptor impedes transport to cell surface in WHHL rabbit, *Science* 232:1230–1237 (1986); Hobbs et al, The LDL receptor locus in familial hypercholesterolemia: mutational analysis of a membrane protein, *Ann Rev Genetics* 24:133–170 (1990)). Consequently, they can not participate in the internalization of plasma LDL-bound cholesterol. Pharmacologic treatments which liberate these mis-folded LDL receptors from the ER and allowed them to proceed to the cell surface might allow them to function properly in cholesterol metabolism and prevent the formation of atherosclerotic plaques.

Tay-Sachs Disease

A number of human diseases have been traced to genetic deficiencies in specific lysosomal hydrolases (Griffiths et al., The Mannose-6-Phosphate Receptor and the Biogenesis of Lysosomes, *Cell* 52:329–341 (1988)). Children who suffer from Tay-Sachs disease, for example, carry a homozygous mutation in the gene encoding the lysosomal enzyme hexosaminidase A. Consequently, their lysosomes are unable to degrade substances containing certain specific sugar linkages. Since they can not be broken down, these substances accumulate in lysosomes. Over time they come to fill the lysosomes, which swell and crowd the cytoplasm. The resulting derangements of cellular function are toxic to a number of cell types and ultimately underlie this disease's uniform fatality within the first few years of life. At least one mutation which has been shown to induce Tay-Sachs disease leads to deletion of the last 22 amino acids of the protein, preventing its proper folding (Lau M M H and Neufeld E F, A frameshift mutation in a patient with Tay-Sachs disease causes premature termination and defective intracellular transport of the alpha-subunit of beta-hexosaminidase, *J Biol Chem* 264:21376–21380 (1989)). The mutant protein is retained in the ER and does not travel to its site of functional residence in the lysosome. Releasing this protein from the ER might prevent the Tay-Sachs pathology in patients who carry this allele.

Immune Surveillance of Tumors and Virally Infected Cells

In order for the immune system to detect and destroy tumor cells and virally infected cells, these target cells must present peptide fragments derived from tumor or viral antigens at their cell surfaces in association with MHC class I molecules. These peptide fragments are derived from proteasome-mediated digestion of the foreign antigens followed by TAP-mediated transport of these fragments into the lumen of the ER, where they can assemble with MHC class I and β2-microglobulin to form the mature MHC complex. Only the mature, peptide-containing MHC complex can depart the ER and be transported to the cell surface. In the absence of peptides in the lumen of the ER, the incompletely assembled MHC I-β2-microglobulin complex is retained in the ER through interactions with calnexin.

Several viruses and tumors avoid immune detection by blocking the surface expression of the mature MHC class I complex. The herpes simplex virus induces host cells to synthesize the ICP47 protein, which directly inhibits the TAP transporter (Hughes E, Hammond C and Cresswell P, Mis-folded major histocompatibility complex class I heavy chains are translocated into the cytoplasm and degraded by the proteasome, *PNAS* 94:1896–1901 (1997)). In a number of tumors, expression of the genes encoding the two polypeptides which constitute the TAP transporter is lost (Pogador et al., Natural killer cell lines kill autologous β2-microglobulin-deficient melanoma cells: Implications for cancer immunotherapy, *PNAS* 94:13140–13145 (1997)). Consequently, the immune system is unable to respond adequately to the pathologic condition. To assist the immune system in recognizing and destroying virally infected or transformed cells, it might be desirable to release the peptide-free MHC class I-β2-microglobulin complex from calnexin-mediated ER retention. This complex would then travel to the cell surface, where it could associate with a specific peptide, administered to the patient by infusion and chosen to maximize the immunogenicity of the resulting peptide-MHC-class I-β2-microglobulin complex. Thus, drugs which release mis-assembled proteins from the ER might prove efficacious in the treatment of a variety of viral and neoplastic diseases.

Hereditary Myeloperoxidase Deficiency

Phagocytes, in particular neutrophils, respond to stimulation with a burst of oxygen consumption. The oxygen consumed is converted to hydrogen peroxide by myeloperoxidase (MPO), which is released from the neutrophil granules, and a complex is formed that is capable of oxidizing a large variety of substances, and that has, as a result, important anti-microbial properties (Klebanoff, Myeloperoxidase, Proc. Assoc. Am. Physicians, 111(5):383–389, 1999).

In the endoplasmic reticulum, MPO precursors interact transiently with calreticulin and calnexin, presumably as molecular chaperones. MPO deficiency is a relatively common disorder, and several missense mutations have been identified where the mutant precursor is retained in the endoplasmic reticulum due to prolonged binding to calnexin. The mis-folded protein is eventually degraded (Nauseef, *Quality Control in the Endoplasmic Reticulum: Lessons from Hereditary Myeloperoxidase Deficiency*, J. Lab. Clin. Med., 134(3):215–221 (1999)). Here as well, a treatment that would allow the protein to exit the ER might restore anti-bacterial phagocytic function to individuals suffering from MPO deficiency.

Congenital Insulin Resistance

The hormone binding site of the insulin receptor is contained in the extracellular region of the protein. In this form of type A insulin resistance, substitution mutations of residues located in the beta-sheet and at the hormone-binding region completely disrupt intracellular folding and movement of the protein, resulting in aberrant retention at an incorrect cellular location.

Misfolded receptors remain bound to calnexin molecules in the endoplasmic reticulum until they are degraded (Rouard et al., *Congenital Insulin Resistance Associated with a Conformational Alteration in a Conserved Beta-Sheet in the Insulin Receptor L1 Domain*, J.Biol. Chem. 274(26):18487–18491 (1999)).

As previously discussed in connection with other diseases, a treatment providing release and cellular export of the mutant receptor could have wide-spread therapeutic use.

I. Thapsigargin

General Description

Thapsigargin and related sesquiterpene lactones are naturally-occurring compounds known to selectively inhibit all of the SERCA ATPases, a family of $Ca^{+2}$-pumping ATPases present in the ER of all mammalian cells, with subnanomolar potency (Lytton et al., *J. Biol. Chem.* 266:17067–17071 (1991)). These inhibitors have no effect on the $Ca^{+2}$-ATPase of the plasma membrane or on other P-type ATPases. Members of this class of inhibitors include thapsigargin and thapsigargicin, both isolated from *Thapsia garganica*, thapsivillosin A (TvA), isolated from *Thapsia villosa*, and trilobolide, extracted from *Laser trilobum* (Wictome et al., *Biochem. J.* 310:859–868 (1995)).

Functional Role

Thapsigargin appears to induce a conformational state of the pump in which several of the partial reactions (e.g., $Ca^{+2}$ binding, $Ca^{+2}$-independent phosphorylation by $P_i$, nucleotide binding) are blocked (Inesi et al., *Arch. Biochem. Biophys.* 298:313–317 (1992)). Studies utilizing a series of thapsigargin analogues indicated that the compound fits into a sterically discriminating cleft involving the hydrophobic transmembrane region of the ATPases (Christensen et al., *Federation of European Biochemical Societies* 335(3):345–348 (1993)).

Clark et al. (*J. Orthop. Res.* 12(5):601–611 (1994)) reported that "the calcium-mobilizing agents thapsigargin and 2,5-di-(tert-butyl)-1,4-benzohydroquinone were shown to markedly elevate the intracellular calcium concentration of chick embryo chondrocytes in a dose-dependent manner." The observed effects of the two compounds on secretion of chondrocyte proteins, including collagen and proteoglycan, was speculated as being due to the specific depletion of the calcium sequestered in the ER.

Addition of 2 mmol/liter $Ca^{+2}$ to thapsigargin-treated CFPAC-1 cells produced a sustained increase of $Cl^-$ and $K^+$ currents, which was reversed by $Ca^{+2}$ removal (Galietta et al., *Pflugers Arch.* 426(6):534–541 (1994)). The researchers concluded "that CFPAC-1 cells respond to nucleotide receptor activation with a transient increase in intracellular $Ca^{+2}$ concentration that stimulates $Ca^{+2}$-dependent $Cl^-$ and $K^+$ currents."

It should be noted that it would not be obvious that long term exposure to thapsigargin will increase functional expression of CFTR. For example, down-regulation of CFTR gene expression was observed by others after exposure of HT-29 human colon carcinoma cells to: (1) agents which increase intracellular divalent cation concentrations (e.g., agents such as the divalent cation ionophores A23187 and ionomycin); (2) thapsigargin; and, (3) growth media containing increased extracellular concentrations of $Ca^{+2}$ or $Mg^{+2}$ (Bargon et al., *Mol. Cell. Biol.* 12(4):1872–1878 (1992)). These researchers stated that thapsigargin was "an agent that releases $Ca^{+2}$ from intracellular stores" resulting in a higher intracellular level of divalent cation concentration. The authors concluded that "despite the independence of $Ca^{+2}$-dependent $Cl^-$ channels and cyclic AMP-dependent CFTR-related $Cl^-$ channels in epithelial cells, increases in intracellular divalent cation concentrations down-regulate the expression of the CFTR gene at the transcriptional level, with consequent decreases in CFTR mRNA and protein."

Exposure of tumor sections from BALB/Urd mice to ionomycin or thapsigargin resulted in a concomitant efflux of $^{125}I$, $^{36}C$ and $^{86}Rb$ (Basavappa et al., *Gastroenterology* 104(6):1796–1805 (1993)).

J. Recombinant DNA

In accordance with the present invention, as described above or as discussed in the Examples below, there may be employed conventional molecular biology, microbiology and recombinant DNA techniques. Such techniques are explained fully in the literature. See for example, Sambrook et al., *Molecular Cloning: A Laboratory Manual* (Second Ed., Cold Spring Harbor Press, Cold Spring Harbor N.Y., 1989); *DNA Cloning: A Practical Approach*, vol. 1 and 2 (D. N. Glover ed., 1985); *Oligonucleotide Synthesis* (M. J. Gait ed., 1984); *Nucleic Acid Hybridization* (B. D. Hames et al., 1985); *Transcription and Translation* (B. D. Hames et al., eds, 1984); E. Harlow et al., *Antibodies: A Laboratory Manual* (Cold Spring Harbor Press, Cold Spring Harbor N.Y., 1988); Roe et al., *DNA Isolation and Sequencing: Essential Techniques* (John Wiley & Sons, New York, 1996) and Ausubel et. al., *Current Protocols in Molecular Biology* (Greene Publishing Co. New York, 1995) to name a few.

For recombinant procedures related to treating cystic fibrosis see, for example, U.S. Pat. Nos. 5,602,110, 5,674, 898 and 5,707,855.

K. Antisense RNA

Antisense molecules are RNA or single-stranded DNA molecules with nucleotide sequences complementary to a specified mRNA. When a laboratory-prepared antisense molecule is injected into cells containing the normal mRNA transcribed by a gene under study, the antisense molecule can base-pair with the mRNA, preventing translation of the mRNA into protein. The resulting double-stranded RNA or RNA/DNA is digested by enzymes that specifically attach to such molecules. Therefore, a depletion of the mRNA occurs, blocking the translation of the gene product so that antisense molecules find uses in medicine to block the production of deleterious proteins. Methods of producing and utilizing antisense RNA are well known to those of ordinary skill in the art (see, for example, C. Lichtenstein and W. Nellen (Editors), *Antisense Technology: A Practical Approach*, Oxford University Press (December, 1997); S. Agrawal and S. T. Crooke, *Antisense Research and Application* (Handbook of Experimental Pharmacology, Volume 131), Springer Verlag (April, 1998); I. Gibson, *Antisense and Ribozyme Methodology: Laboratory Companion*, Chapman & Hall (June, 1997); J. N. M. Mol and A. R. Van Der Krol, *Antisense Nucleic Acids and Proteins*, Marcel Dekker; B. Weiss, *Antisense Oligodeoxynucleotides and Antisense RNA: Novel Pharmacological and Therapeutic Agents*, CRC Press (June, 1997); Stanley et al., *Antisense Research and Applications*, CRC Press (June, 1993); C. A. Stein and A. M. Krieg, *Applied Antisense Oligonucleotide Technology* (April, 1998)).

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding UGGT. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2'O-methyl rather than phosphodiesterase linkages within the backbone of the molecule. This concept can be extended by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

L. High-Throughput Screening

The power of high throughput screening is utilized in the search for new compounds (in addition to thapsigargin) which are capable of mobilizing mis-folded or incompletely assembled proteins from the ER, thus enabling their surface delivery. The following protocol is designed to permit rapid automated screening of large numbers of compounds useful for practicing the claimed invention. The demonstration that thapsigargin produces a positive result when tested in the high-throughput screening assays will act as a positive control. For general information on high-throughput screening, see, for example, *Cost-Effective Strategies for Automated and Accelerated High-Throughput Screening*, IBCS Biomedical Library Series, IBC United States Conferences (February, 1996); John P. Devlin (Editor), *High Throughput Screening*, Marcel Kedder (1998); U.S. Pat. No. 5,763, 263.

CTL-Mediated Cell Lysis

Cytotoxic T cells recognize their targets through interactions with Major Histocompatibility Complex (MHC) class I proteins expressed on the target cell surfaces. MHC class I is a complex composed of the MHC class I heavy chain (a transmembrane protein) and β2-microglobulin (β2m). MHC class I heavy chains assemble with β2m during their post-synthetic residence in the ER. Each MHC class I heavy chain also binds to a peptide produced by cytosolic proteolysis catalyzed by the proteasome and transported into the lumen of the ER by the ATP-dependent transporter associated with antigen processing (TAP). The complete MHC class I heavy chain-β2m-peptide complex must be fully assembled before it can depart the ER and be delivered to the cell surface. In the absence of β2m or of peptide, MHC class I is retained in the ER and is unavailable for recognition by T cells.

For general information on the Major Histocompatibility Complex, see, for example, Srivastava et al., *Immunogenetics of the Major Histocompatibility Complex*, Vch Pub. (March, 1991); B. Pernis and H. J. Vogel, *Cell Biology of the Major Histocompatibility Complex*, Academic Press (October, 1995); T. W. Mak and J. Simard, *Handbook of Immune Response Genes*, Plenum Pub. Corp. (February, 1998); R. E. Humphreys and S. K. Pierce, *Antigen Processing and Presentation*, Academic Press (August, 1994); J. Klein and D. Klein, *Molecular Evolution of the Major Histocompatibility Complex*, NATO Asi Series, Series H, Cell Biology, Vol. 59, Springer Verlag (January, 1992); L. B. Schook and S. J. Lamont, *The Major Histocompatibility Complex Region of Domestic Animal Species*, CRC Series in Comparative Immunology, CRC Press (September, 1996); U.S. Pat. Nos. 5,364,762, 5,639,458 and 5,734,023.

The 0.174 line of lymphoblastoid cells (hereinafter, 'the 0.174 cells') carries a mutation that eliminates the function of the TAP transporter (DeMars et al., Mutations that impair a posttranscriptional step in expression of HLA-A and -B antigens, *PNAS* 82:8183–8187 (1985); Hughes E, Hammond C and Cresswell P, Mis-folded major histocompatibility complex class I heavy chains are translocated into the cytoplasm and degraded by the proteasome, *PNAS* 94:1896–1901 (1997)). Consequently, proteasome-processed peptides are not available for assembly with MHC class I molecules in these cells. As a result, most MHC class I molecules (with the exception of those which can assemble with signal sequence peptides) are retained in the ER.

An assay based on cytotoxic T lymphocyte (CTL)-mediated cell lysis is used to identify compounds which permit MHC class I molecules to be released from the ER and expressed at the surface of 0.174 cells. A line of 0.174 cells expressing a specific MHC class I allele will be prepared by standard cDNA transfection techniques. CTL's which recognize a specific antigenic peptide in association with this class I allele will also be prepared by standard techniques (Yap K and Ada G, Cytotoxic T cells specific for influenza virus-infected target cells, *Immunology* 32: 151–159 (1977)). The 0.174 cells will be aliquoted into the wells of a 96 well cell culture plate. Each well will receive a quantity of a compound to be tested, after which they will be incubated for 90 minutes at 37° C. The 96 well plates will be centrifuged to pellet the 0.174 cells, after which the cells will be resuspended in normal media without any added test compound. The media will contain the specific antigenic peptide. After a further two hour incubation at 37° C., CTLs will be added to each well. Cell lysis will be measured using a standard automated fluorometric assay for T cell toxicity (Brenan M and Parish C. Automated fluorometric assay for T cell toxicity. *J Immuno*. Methods 112:121–131, 1988). Any well which has received a compound that permits the incompletely assembled MHC class I-β2M complex to depart the ER, reach the cell surface and bind the antigenic peptide present in the medium will be susceptible to CTL-mediated lysis. A duplicate 96 well assay plate will receive the same chemical compounds but will not receive CTL cells. Detection of cell lysis on this duplicate plate will identify compounds which lyse cells directly, rather than through the MHC-mediated pathway. This assay will permit rapid and reliable identification of compounds which permit the release of incompletely assembled or mis-folded proteins from the ER. Furthermore, the assay is designed to be employed in the high throughput screening of libraries consisting of natural products or of combinatorially synthesized chemicals.

Immunodiagnostics/Immunoassays

This group of techniques is used for the measurement of specific biochemical substances, commonly at low concentrations in complex mixtures such as biological fluids, that depend upon the specificity and high affinity shown by suitably prepared and selected antibodies for their complementary antigens. A substance to be measured must, of necessity, be antigenic—either an immunogenic macromolecule or a haptenic small molecule. To each sample a known, limited amount of specific antibody is added and the fraction of the antigen combining with it, often expressed as the bound:free ratio, is estimated, using as indicator a form of the antigen labeled with radioisotope (radioimmunoassay), fluorescent molecule (fluoroimmunoassay), stable free radical (spin immunoassay), enzyme (enzyme immunoassay), or other readily distinguishable label.

Antibodies can be labeled in various ways, including: enzyme-linked immunosorbent assay (ELISA); radioimmuno assay (RIA); fluorescent immunoassay (FIA); chemiluminescent immunoassay (CLIA); and labeling the antibody with colloidal gold particles (immunogold).

Common assay formats include the sandwhich assay, competitive or competition assay, latex agglutination assay, homogeneous assay, microtitre plate format and the microparticle-based assay.

Enzyme-linked Immunosorbent Assay (ELISA)

ELISA is an immunochemical technique that avoids the hazards of radiochemicals and the expense of fluorescence detection systems. Instead, the assay uses enzymes as indicators. ELISA is a form of quantitative immunoassay based on the use of antibodies (or antigens) that are linked to an insoluble carrier surface, which is then used to 'capture' the relevant antigen (or antibody) in the test solution. The antigen-antibody complex is then detected by measuring the activity of an appropriate enzyme that had previously been covalently attached to the antigen (or antibody).

For information on ELISA techniques, see, for example, J. R. Crowther, *Elisa: Theory and Practice* (*Methods in Molecular Biology*, Vol. 42), Human Pr. (1 995); Challacombe and Kemeny, *ELISA and Other Solid Phase Immunoassays: Theoretical and Practical Aspects*, John Wiley & Son Ltd. (1998); D. M. Kemeny, *A Practical Guide to Elisa*, Pergamon Pr. (1991); and E. Ishikawa, *Ultrasensitive and Rapid Enzyme Immunoassay* (*Laboratory Techniques in Biochemistry and Molecular Biology*, V. 27), Elsevier Advanced Technology (1991).

Colorimetric Assays for Enzymes

Colorimetry is any method of quantitative chemical analysis in which the concentration or amount of a compound is determined by comparing the color produced by the reaction of a reagent with both standard and test amounts of the compound, often using a colorimeter. A colorimeter is a device for measuring color intensity or differences in color intensity, either visually or photoelectrically.

Standard colorimetric assays of beta-galactosidase enzymatic activity are well known to those skilled in the art (see, for example, Norton et al., Molecular & Cellular Biology 5:281–290 (1985)). A colorimetric assay can be performed on whole cell lysates using O-nitrophenyl-beta-D-galactopyranoside (ONPG, Sigma, St. Louis, Mo.) as the substrate in a standard colorimetric beta-galactosidase assay (Maniatis et al., Cold Spring Harbor, N.Y., Cold Spring Harbor Lab. (1990)). Automated colorimetric assays are also available for the detection of beta-galactosidase activity, as described in U.S. Pat. No. 5,733,720.

Immunofluorescence Assays

Immunofluorescence or immunofluorescence microscopy is a technique in which an antigen or antibody is made fluorescent by conjugation to a fluorescent dye and then allowed to react with the complementary antibody or antigen in a tissue section or smear. The location of the antigen or antibody can then be determined by observing the fluorescence by microscopy under ultraviolet light.

For general information on immunofluorescent techniques, see, for example, Knapp et al., Immunofluorescence and Related Staining Techniques, Elsevier/North-Holland Biomedical Press (1978); V. J. Allan, *Protein Localization by Fluorescent Microscopy: A Practical Approach* (The Practical Approach Series, 218), Oxford Univ. Press (1999); E. H. Beutner, *Defined Immunofluorescence and Related Cytochemical Methods*, New York Academy of Sciences (1983); and E. O. Caul, *Immunofluorescence Antigen Detection Techniques in Diagnostic Microbiology*, Cambridge Univ. Press (1993). For detailed explanations of immunofluorescent techniques applicable to the present invention, see, U.S. Pat. Nos. 5,912,176; 5,869,264; 5,866,319; and 5,861,259.

J. Combinatorial Chemistry

Combinatorial chemistry can be utilized to generate compounds which are chemical variations of compounds useful in the present invention. Such compounds can be evaluated using the high-throughput screening methods of the present invention.

Basic combinatorial chemistry concepts are well known to one of ordinary skill in the chemical arts and can also be found in Nicholas K. Terrett, *Combinatorial Chemistry* (*Oxford Chemistry, Masters*), Oxford Univ. Press (1998); Anthony W. Czarnik and Sheila Hobbs Dewitt (Editors), *A Practical Guide to Combinatorial Chemistry*, Amer. Chemical Society (1997); Stephen R. Wilson (Editor) and Anthony W. Czarnik (Contributor), *Combinatorial Chemistry: Synthesis and Application*, John Wiley & Sons (1997); Eric M. Gordon and James F. Kerwin (Editors), *Combinatorial Chemistry and Molecular Diversity in Drug Discovery*, Wiley-Liss (1998); Shmuel Cabilly (Editor), *Combinatorial Peptide Library Protocols* (*Methods in Molecular Biology*), Human Press (1997); John P. Devlin, *High Throughput Screening*, Marcel Dekker (1998); Larry Gold and Joseph Alper, Keeping pace with genomics through combinatorial chemistry, Nature Biotechnology 15, 297 (1997); Aris Persidis, Combinatorial chemistry, Nature Biotechnology 16, 691–693 (1998).

K. Modifying Thapsigargin, Cyclopiazonic Acid and DBHQ to Increase Therapeutic Efficacy Thapsigargin, cyclopiazonic acid and 2,5-di-(tert-butyl)-1,4-hydroquinone (DBHQ) inhibit the ER Ca-ATPase, resulting in the transient elevation of cytosolic calcium levels and the depletion of ER calcium stores. While this activity underlies the proposed therapeutic benefit of these three compounds in CF, it is possible that it may also produce toxic side effects by activating calcium-dependent processes in a wide variety of cells. Since the primary affected organ in CF is the lung, correction of the CF defect in airway epithelial cells would dramatically reduce the morbidity associated with this disease. It would be desirable, therefore, to construct derivatives of these compounds which could be applied locally to the airway by aerosol inhalation and which would not diffuse out of the airway epithelial cells to enter the systemic circulation. Such derivatives would be much less likely to exhibit systemic toxic side effects.

A non-specific esterase activity is present in the cytoplasm of most eukaryotic cell types. This activity has been exploited in the design of numerous compounds whose purpose is to enter the cytoplasm of target cells and subsequently remain trapped there. These compounds, which include several indicator dyes used to measure intracellular ionic concentrations, are synthesized as acetoxymethylesters (Grynkiewicz G, Poenie M and Tsien RY, A new generation of Ca indicators with greatly improved fluorescence properties, *J. Biol. Chem.* 260:3440–3450 (1985)). In this form they are membrane permeant and can diffuse across the cell membrane to enter the cytoplasm. The action of the cytoplasmic esterase removes methanol groups, leaving behind negatively charged carboxylic acid residues on the compound of interest. In this charged state, the compound is no longer membrane permeant and it is thus trapped in the cytosol.

Thapsigargin, cyclopiazonic acid and DBHQ may be modified to incorporate acetoxymethylester groups. These modified compounds would then be administered by aerosol inhalation. Presumably, they would enter the surface airway epithelial cells by diffusing across their apical plasma membranes. Once inside the airway epithelial cells, they would become substrates for the action of the cytoplasmic esterase. Esterase action on the derivatized compounds would leave these compounds with negatively charged carboxylic acid residues, thus preventing their departure from the airway epithelial cells. Consequently, the compounds would only gain access to and exert effects upon airway epithelial cells, which are their intended target. The potential for systemic side effects would thus be greatly reduced.

This strategy will succeed only if the addition of one or more carboxylic acid groups to thapsigargin, cyclopiazonic acid or DBHQ does not markedly reduce their inhibitory effects on the ER Ca-ATPase. No modifications may be necessary to reduce the toxicity of at least some of these compounds. Animal toxicity has not been associated with DBHQ (Chao et al., Calcium- and CaMKII-dependent chloride secretion induced by the microsomal Ca-ATPase inhibitor 2,5-di-(tert-butyl)-1,4-hydroquinone in cystic fibrosis pancreatic epithelial cells, *J. Clin. Invest.* 96:1794–1801 (1995)).

L. Pharmaceutical Preparations

General

The therapeutics compositions of this invention can be used in the form of a medicinal preparation, for example, in solid, semi-solid or liquid form which contains the composition of the present invention, as an active ingredient, in admixture with an organic or inorganic carrier or excipient suitable for external, enteral or parenteral applications. The active ingredient may be compounded, for example, with the usual non-toxic pharmaceutically acceptable carriers for tablets, pellets, capsules, inhalants, suppositories, solutions, emulsions, suspensions, and any other form suitable for use. Formulations of the present invention encompass those which include carriers such as water, talc, glucose, lactose, gum acacia, gelatin, mannitol, starch paste, magnesium trisilicate, corn starch, keratin, colloidal silica, potato starch, urea and other carriers suitable for use in manufacturing preparations, in solid, semisolid or liquid form and in addition auxiliary, stabilizing, thickening and coloring agents and perfumes may be used.

Solid Compositions

For preparing solid compositions such as tablets or capsules, the principal active ingredients are mixed with a pharmaceutical carrier (e.g., conventional tableting ingredients such as corn starch, lactose, sucrose, sorbitol, talc, stearic acid, magnesium stearate, dicalcium phosphate or gums) and other pharmaceutical diluents (e.g., water) to form a solid preformulation composition containing a substantially homogeneous mixture of a composition of the present invention, or a non-toxic pharmaceutically acceptable salt thereof. When referring to the preformulation compositions as substantially homogenous, it is meant that the active ingredients are dispersed evenly throughout the composition so that the composition may be readily subdivided into equally effective unit dosage forms such as tablets, pills and capsules. This solid preformulation composition is then subdivided into unit dosage forms of appropriate amounts.

The tablets or pills of the novel composition can be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol and cellulose acetate.

The active compounds may also be formulated in rectal compositions such as suppositories or retention enemas, e.g., containing conventional suppository bases such as cocoa butter or other glycerides.

Inhalants

For intranasal administration or administration by inhalation, the active compounds are conveniently delivered in the form of a solution or suspension from a pump spray container that is squeezed or pumped by the patient, or as an aerosol spray presentation from a pressurized container or nebulizer, with the use of a suitable propellant (e.g., dichlorodifluoromethane, trichlorofluoromethane, dichlorotetrafluoroethane, carbon dioxide or other suitable gas). In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of an active compound and a suitable powder base such as lactose or starch.

Thapsigargin treatment leads to acute elevations of cytosolic calcium concentrations in a wide variety of cell types (Hofer and Machen, *Proc. Nat. Acad. Sci.* 90:2598–2602 (1993)). Since release of calcium from intracellular stores acts as a second messenger controlling an enormous list of critical cellular processes, including muscle contraction, hormone secretion and neuronal communication (Berridge, *Mol. Cell. Endocrin.* 98:119–24 (1994)) it is perhaps surprising that thapsigargin is so well tolerated when administered in nebulized form. The chemical structure of thapsigargin includes 3 ester groups (Christensen et. al, *FEBS Lett.* 335:345–348 (1993)). The cytoplasm of most eukaryotic cells is richly endowed with non-specific esterase activity, which has been shown to rapidly de-esterify xenobiotic compounds that enter the cells by diffusion (Tsien et al., *J. Cell Biol.* 94:325–334 (1982)). It is likely, therefore, that after entering airway epithelial cells by diffusion across their apical membranes, thapsigargin is modified by the esterase activity. Loss of the ester groups reduces thapsigargin's efficacy as a calcium pump inhibitor by at least 40-fold (Christensen et. al., supra). Thus thapsigargin may possess the desirable pharmacologic characteristic of being converted at its target organ into an inactive metabolite.

If this is indeed the case, thapsigargin can be applied locally to the airway by aerosol inhalation and does not diffuse out of the airway epithelial cells to enter the systemic circulation in a bioactive form. Future derivatives that exploit this feature might be even less likely to exhibit systemic toxic side effects. It is also interesting to note that no toxicity may be associated with at least some compounds that should mimic the desired thapsigargin effect. No animal toxicity has been attributed to DBHQ, a compound that shares thapsigargin's ability to inhibit ER Ca-ATPase activity. (Chao et al., *J. Clin. Invest,* 96:1794–1801 (1995)).

Finally, other classes of compounds in addition to calcium pump inhibitors are also likely to be of potential therapeutic utility in treating clinical conditions associated with ER retention of mis-folded proteins. Any compound which directly inhibits the function of the ER retention chaperone machinery or which alters the environment of the ER lumen so that these proteins can not function properly may possess potential clinical value.

Liquid Forms

The liquid forms, in which the novel composition of the present invention may be incorporated for administration orally or by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

Buccal Administration

For buccal administration, the composition may take the form of tablets or lozenges formulated in conventional manners.

The active compounds may be formulated for parenteral administration by injection, which includes using conventional catheterization techniques or infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulating agents such as suspending, stabilizing, and/or dispersing agents. Alternatively, the active ingredients may be in powder form for reconstitution with a suitable vehicle, e.g., sterile pyrogert-free water, before use.

Formulations

Formulations of the compounds of this invention are prepared for storage or administration by mixing the compound having a desired degree of purity with physiologically acceptable carriers. excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Without further description, it is believed that one of ordinary skill in the art, using the preceding description and the following illustrative examples, can make and utilize the compounds of the present invention and practice the claimed methods.

EXAMPLES

The following working examples which disclose UGGT regulation, specifically point out preferred embodiments of the present invention. These examples are not to be construed as limiting in any way the scope of the invention. Other examples involving UGGT regulation as well as other proteins that regulate intracellular targeting of mis-folded proteins will be apparent to the skilled artisan. Assays analogous to those described below can be utilized in examining other agents that regulate UGGT or other proteins that regulate mis-folded proteins.

Tissue Culture/Cell Lines

IB3-1 (Zeitlin et al., 1991) and $\Sigma$CFBE290$^-$ (Kunzelman et al., *Am. J. Resp. Cell. Mol. Biol.* 8:522–529.(1993)) cells are CF-affected airway epithelial cell lines. Both IB3-1 and $\Sigma$CFBE290$^-$ are immortalized, well-characterized human bronchial epithelial cell lines derived from CF-patients. The cell lines retain the diagnostic feature of CF-affected epithelial cells: a lack of cAMP-stimulated, PKA-activated Cl$^-$ channel activity. Genotypically, IB3-1 is a compound heterozygote containing the $\Delta$F508 mutation and W1282X, a nonsense mutation with a premature termination signal. The W1282X mutation does not result in a stable mRNA and yields no protein (Hamosh et al., *Hum. Mol. Gen.* 1:542–544.(1992)). Therefore, the only stable CFTR protein produced in the IB3-1 cells is the $\Delta$F508 product.

The $\Sigma$CFBE290$^-$ cell line is derived from a patient homozygous for the $\Delta$F508 mutation. Both cell lines were grown at 37° in 5% $CO_2$. The IB3-1 cells were maintained in LHC-8 media (Biofluids) supplemented with 5% fetal calf serum, tobramycin (20 ug/ml), penicillin (100 U/ml), streptomycin (100 ug/ml). The $\Sigma$CFBE290$^-$ cells were maintained in Dulbecco's Modified Eagles medium (DMEM) supplemented with 10% fetal calf serum, tobramycin (20 ug/ml), penicillin (100 U/ml), and streptomycin (100 ug/ml).

The CFPAC-1 cell line is a ductal pancreatic adenocarcinoma cell line derived by differential trypsinization of explant cultures from a metastatic lesion in the liver of a 26 year old male with CF (Schoumacher et al., *Proc. Natl. Acad. Sci.* 87:4012–4016 (1990)). The cell line is homozygous for expression of $\Delta$F508 CFTR and has the ion transport properties of CF-affected epithelia. CFPAC-1 cells show epithelial morphology and polarization with apical microvilli.

CFPAC cells were grown at 37° in 5% $CO^2$ and maintained in Isocove's modified Dulbucco's medium supplemented with 10% fetal calf serum. Both for measurements of short circuit current and for immunofluorescence experiments, these cells were grown on collagen coated permeable supports (Transwell Snapwell filter cups, Corning Costar, Cambridge, Mass.). The well characterized T84 intestinal epithelial cell line was grown according to standard methods (Cohn et al., *Proc. Nat. Acad. Sci.* 89:2340–2344.(1992); Bell and Quinton, *Am. J. Physiol.* 262:C555–C562.(1992)) and were also plated on permeable supports for short circuit current assays.

Experiment 1

Patch Clamp Analysis

Materials and Methods

Single channel patch clamp studies were performed using conventional procedures on the CF-affected bronchial epithelial cell lines, IB3-1 and $\Sigma$CFBE290$^-$ (Egan et al., *Am. J. Physiol.* 268:C243–C251 (1995)). Cells were grown in culture flasks on glass chips coated with collagen (150 ug/ml), fibronectin (10 ug/ml), and bovine serum albumin (10 ug/ml).

When cells were at 75% confluence they were incubated with 1 uM thapsigargin (or vehicle alone) for 1.5 hours at 37° C. using the following protocol. First, the LHC-8 media or DMEM was removed from the tissue culture dish and the cells were rinsed with phosphate buffered saline. Fresh LHC-8 media containing 1 uM thapsigargin was added to the cell culture dish. After the 1.5 hour thapsigargin exposure, cells were rinsed with fresh media and allowed to incubate for 2 hours at 37° C. prior to patch clamping. The patch clamp bath solution contained (in mM) 150 NaCl, 2MgCl$_2$, 1 EGTA, 5 HEPES, and 0.5 CaCl$_2$, pH=7.3. The pipette solution contained (in mM) 150 NaCl, 2MgCl$_2$, 5 HEPES, and 2 CaCl$_2$, pH=7.3.

Patch clamp studies were performed at 22–25° C. Data were amplified on an Axopatch 200A patch clamp amplifier and recorded on videotape for later analysis. Data were low pass filtered and digitized at 1 kHz. Data were analyzed using Pclamp6.

Results

The surface expression of ΔF508 CFTR was initially examined by patch clamp analysis performed on two different treated and untreated CF-affected respiratory epithelial cell lines, IB3-1 (Zeitlin et al., *Am. J. Resp. Cell. Mol. Biol.* 4:313–319 (1991)) and ΣCFBE290⁻ (Kunzelman et al., *Am. J. Resp. Cell, Mol. Biol.* 8:522–529 (1993)).

In the untreated CF-affected cells, no low conductance chloride channels could be activated with a cAMP-stimulation cocktail containing IBMX and forskolin (FIG. 1A). These findings are consistent with the primary CF defect. In contrast, treatment with thapsigargin dramatically enhanced the IB3-1 and ΣCFBE290⁻ cells' chloride conductance.

Cells were incubated in 1 μM thapsigargin for 90 minutes, after which they were incubated for 2 hours in the absence of the drug. Patch clamp analysis of the treated cells revealed that their plasma membranes now contained abundant low conductance chloride channel activity (FIG. 1B and Table 1). The biophysical characteristics of the channel activity were consistent with those of the channel formed by the ΔF508 CFTR protein (Dalemans et al., *Nature* 354:526–528 (1991); Egan et al., *Am. J. Physiol.* 268:C243–C251 (1995); Rubenstein et al., *J. Clin. Invest.* 100:2457–2465 (1997); Haws et al., *Am. J. Physiol.* 270:C1544–C1555.(1996); Hwang et al., *Am J Physiol.* 273:C988–998 (1997)). Thus, the current versus voltage relationship is linear (FIG. 2A), revealing an average single channel conductance of 11.8 pS. Furthermore, analysis of an open state histogram (FIG. 2B) produces a calculated $P_0$ of 0.12. Channel activity could be inhibited by glibenclamide (data not shown). The levels of functional expression achieved through the manipulation (Table 1) are in line with the level of expression that has been suggested to be required to reverse the cystic fibrosis defect (Johnson et al., Nature Gen. 2:21–25(1992)).

Patch clamp experiments were also carried out on thapsigargin-treated cells after they were allowed to incubate for 8 hours or 24 hours following a single thapsigargin exposure to determine how long the effect of this treatment on the expression of the CFTR-like channel could persist. After an 8 hour recovery period CFTR-like channel activity was observed in 7 of 20 excised patches (35%). However after a 24 hour recovery period 0 of 10 patches (0%) demonstrated any CFTR-like channel activity.

Treatment with calcium pump inhibitors leads to a transient rise in intracellular calcium concentrations, which has been shown to acutely stimulate chloride currents in CF epithelial cells (Chao et al., *J. Clin. Invest.* 96:1794–1801 (1995)). To ascertain if the change in CFTR channel activity was due to this short term effect of thapsigargin, cells were treated with a short exposure to thapsigargin (15 minutes) and then allowed to recover for 2 hours prior to patch clamping. No CFTR-like channel activity was stimulated in 10 patches following this protocol (data not shown), suggesting that short-term elevations of intracellular calcium concentrations that follow treatment with thapsigargin do not result in detectable long term increases in CFTR-like channel activity.

TABLE 1

| Cell Type | Incubation Condition | Patches with CFTR channel [activity] |
| --- | --- | --- |
| IB3-1 | control, no treatment | 0/10 (0%) (in previous studies 0/35) |
| ΣCFBE290⁻ | control, no treatment | 0/8 (0%) |
| IB3-1 | thapsigargin treated | 25/76 (32.8%) |
| ΣCFBE290⁻ | thapsigargin treated | 8/24 (33.3%) |
| Combined | control, no treatment | 0/28 (0%) |
| Combined | thapsigargin treated | 33/100 (33%) |

[1] Note: Normally in unaffected airway epithelial cells CFTR channel activity can be detected via patch clamp techniques in 70% of patches.

Experiment 2
Short Circuit Current Measurements
Materials and Methods

CFPAC-1 or T84 cells were grown on collagen coated permeable supports (Transwell Snapwell filter cups, Coming Costar, Cambridge, Mass.). Cells were fed every one to two days from the basolateral surface of the monolayer while the apical surface was exposed to the humidified 5% CO$_2$ environment. Filters were cultured until a tight monolayer was achieved.

Prior to electrical studies some of the monolayers were treated with 1 uM thapsigargin using the following protocol. Culture media containing 1 uM thapsigargin was added to the apical surface of the monolayer and incubated for 1.5 hours at 37° C. Cells were then rinsed with fresh thapsigargin-free media and allowed to incubate for 2 hours at 37° C., after which they were used for Ussing chamber studies. The Ussing chamber bath solution was a nominally bicarbonate-free Ringer's solution that was composed of (in mM) 140 NaCl, 1.2 MgCl$_2$, 5 K$_2$HPO$_4$, 0.5 KH$_2$PO$_4$, 5 HEPES, 1.2 CaCl$_2$, and 5 glucose pH=7.4. Bath solutions were warmed to 37° C.

Ag—AgCl wires were embedded in 3M KCl agar bridges were used as voltage and current electrodes on each side of the monolayer contained in an Ussing chamber system (World Precision Instruments, WPI). Voltage was clamped using an EC-825 voltage clamp amplifier (Warner Instruments) with a digital current and voltage readout. The transepithelial potential difference ($V_{te}$) is continuously recorded. At 5-minute intervals the $V_{te}$ is clamped to 0 and the short circuit current ($I_{SC}$) was determined. Under $I_{sc}$ conditions a voltage pulse between 20 and 40 mV was applied and the change in current was used to calculate the transepithelial resistance ($R_{te}$).

After cells were mounted in the Ussing chamber electrical parameters were assessed for 20 to 30 minutes (control period). Following the control period a cAMP-stimulating cocktail (10 μM forskolin and 100 μM IBMX) was added to the apical chamber. Electrical parameters were monitored for 20–30 minutes following this treatment to assess for changes in $I_{SC}$, $V_{te}$, and $R_{te}$. Furosemide ($10^{-4}$M), an inhibitor of chloride secretion, was then added to the basolateral bath for 20 minutes to assess its affect on chloride secretion. In the continued presence of furosemide, $10^{-4}$M amiloride, an inhibitor of sodium absorption, was added to the apical bath for 10 minutes. During these maneuvers, electrical parameters were continuously monitored.

Results

To determine whether the thapsigargin effect on CFTR channel activity is of sufficient magnitude to increase epithelial short circuit current, CFPAC-1 cells (Schoumacher et al., *Proc. Natl. Acad. Sci.* 87:4012–4016 (1990)) were grown on collagen-coated permeable supports and examined in Ussing chambers. When monolayers of untreated CFPAC-1 cells were exposed to a cAMP-stimulation there was no increase in the short circuit current (−0.38±1.8%, n=12) (FIG. 3). The lack of response to the elevation of cytosolic cAMP concentrations is consistent with the CF phenotype (Grubb et al., *Am. J. Resp. Cell. Mol. Biol.* 8:454–460 (1993)).

In contrast, when thapsigargin treated CFPAC-1 monolayers were exposed to the cAMP-stimulation cocktail, there was a 14.6±6.6% increase in short circuit current (n=12, p=0.02) which was inhibited by furosemide, suggesting it was due to an increase in net chloride secretion. The presence of the cAMP-stimulated chloride secretion in the thapsigargin-treated CFPAC cells is consistent with a partial correction of the CF ion transport defect and it is similar in magnitude to that seen with T84 cell monolayers (FIG. 3). T84 cells are a human colonic epithelial cell line that expresses high levels of wild-type CFTR (Cohn et al., *Proc. Nat. Acad. Sci.* 89:2340–2344.(1992); Bell and Quinton, *Am. J. Physiol.* 262:C555–C562.(1992)).

Experiment 3
Immunofluorescence Analysis

CFPAC and ΣCFBE290− epithelial cells were grown to confluence on 0.45μTranswell filter inserts (Corning Costar, Cambridge, Mass.) under the same conditions described for the short circuit current measurements. Prior to immunofluorescence analysis, filter grown cell monolayers were treated for 90 min with 1 μM thapsigargin at 37° C., present in both the apical and basolateral media compartments. The media was then changed to standard Iscove's growth medium or DMEM without thapsigargin, and cells were incubated for 2 or 4 hours at 37° C. Control cells underwent the same media changes but were not subjected to thapsigargin treatment.

Following the second incubation, the filter grown monolayers were washed once with phosphate buffered saline supplemented with calcium and magnesium (150 mM NaCl, 10 mM $NaP_i$, pH 7.4, 1 mM $MgCl_2$, 0.1 mM $CaCl_2$), after which they were fixed for 10 minutes in −20° C. 100% methanol. Immunofluorescence labeling was performed using the well characterized 169 and 181 antibodies (gift of W. Guggino, Johns Hopkins University) directed against the R domain and the prenucleotide binding fold of the CFTR protein, respectively (Crawford et al., *Proc. Nat. Acad. Sci.* 88:9262–9266 (1991)) and a monoclonal antibody directed against the α-subunit of the Na,K-ATPase (Gottardi and Caplan, *J. Cell Biol.* 121:283–293 (1993)).

Incubations with primary and rhodamine-conjugated secondary antibodies were performed as previously described (Gottardi and Caplan, Id.). Labeled cells were examined using a Zeiss LSM 410 laser scanning confocal microscope. All images are the product of 8-fold line averaging. Contrast and brightness settings were chosen so that all pixels were in the linear range. XZ cross sections were generated using a 0.2μmotor step.

Results

To examine further the effects of thapsigargin on the subcellular distribution of the ΔF508 protein, we performed immunofluorescent localization of the CFTR protein in treated and untreated CFPAC cells. In untreated cells, CFTR staining is barely detectable in a diffuse cytoplasmic pattern surrounding the nucleus (FIG. 4). This pattern is consistent with the localization of the ΔF508-CFTR protein to the ER in the untreated cells. In treated cells, viewed both en face and in XZ cross section, bright labeling of apical microvilli could be detected in most of the cells. Cells that were incubated for 2 hours following the thapsigargin treatment exhibited only apical staining. No intracellular ER labeling could be detected in these cells. Cells that were incubated for 4 hours following the thapsigargin treatment exhibiting CFTR staining both at the apical membrane and in the ER (data not shown). Thus, treatment with thapsigargin leads to redistribution of the mutant ΔF508-CFTR protein from the ER to the apical membrane.

As evidenced by the pattern observed in cells incubated for 4 hours after the removal of thapsigargin, ΔF508-CFTR protein synthesized following the removal of the drug is retained in the ER. These observations are consistent with the interpretation that thapsigargin treatment permits misfolded ΔF508-CFTR protein to be released from the ER and travel to its appropriate site of functional residence at the apical plasma membrane.

It is likely that the mechanism through which thapsigargin effects the redistribution of the Δ508F CFTR protein from the ER to the cell surface is related to this compound's capacity to reduce the ER's intralumenal $Ca^{++}$ concentration. It is also possible, however, that thapsigargin might interact directly with the ΔF508 CFTR protein to alter its tertiary structure. CFTR is related to the MDR family of ABC transport proteins. Members of the MDR family are capable of interacting with and transporting a wide variety of chemical compounds (Higgins, *Ann. Rev. Cell Biol.* 8:67–113 (1992)). It has been demonstrated that MDR proteins that carry mutations resulting in mis-folding and ER retention can be functionally rescued through exposure to compounds that are substrates for the particular MDR protein's transport activity (Loo and Clarke, *J. Biol. Chem.* 272:709–712 (1997); Loo and Clarke, *J. Biol. Chem.* 273:14671–14674 (1998)). Presumably, binding substrate compounds stabilizes the protein's conformation sufficiently to permit it to elude the ER's quality control machinery.

In light of the homology relating CFTR to the MDR proteins, it is possible that thapsigargin exerts its effect on ΔF508-CFTR through a similar mechanism. If CFTR manifests an MDR-like activity, thapsigargin could conceivably be a substrate analogue whose interaction with a binding site on CFTR could stabilize and modify this protein's structure. According to this model, thapsigargin's effect on calcium pumps and ER lumenal calcium concentrations would not be relevant to its mode of action in rescuing ΔF508-CFTR.

To test this possibility, we exposed ΣCFBE290− cells to the calcium pump inhibitors DBHQ and cyclopiazonic acid, which are structurally unrelated to thapsigargin (Khan et al., *Biochem.* 34:14385–14393 (1995); Whitcome et al., *Biochem. J.* 310:859–868 (1995)). As assayed by immunofluorescence microscopy (data not shown), both compounds were able to recapitulate thapsigargin's capacity to induce ΔF508-CFTR surface delivery. Since DBHQ and cyclopiazonic acid are chemically quite distinct from thapsigargin and from each other, it is likely that their effects on ΔF508-CFTR arise from their shared capacity to release calcium from the ER lumen rather than from any direct interaction with the CFTR protein itself.

Experiment 4
Nebulized Thapsigargin

A nebulization chamber was constructed using an 8 quart plastic container with a lid that creates an air tight seal. A 'T piece nebulizer device' (Hudson RCI T-up Draft Nebumist Nebulizer) was inserted into the container via an opening located on the side of the chamber. The nebulization device was filled with 5 mls of 1 $\mu$M thapsigargin dissolved in physiologic saline solution. The gas source (high pressure air) was attached to the set up to create a flow rate of $\geq 12$ liters per minute. Flow was adjusted to maintain a fine visible mist throughout the chamber. Numerous small ventilation holes were placed at the top of the chamber to ensure the escape of carbon dioxide. The nebulization chamber was kept in a fume hood during the experiments to allow for dispersion of any escaped mist.

Mice or cells were placed into the chamber prior to the onset of nebulization. Mice were observed continuously during the nebulization treatments and observations were documented every 15–30 minutes. Lungs were prepared for histologic analysis according to methods described previously (Courtois-Coutry et al., Cell 90:501–510 (1997)).

Results

Thapsigargin treatment results in the transient elevation of cytosolic calcium levels and the depletion of ER calcium stores (Hofer and Machen, Proc. Nat. Acad. Sci. 90:2598–2602 (1993), Montero et al., J. Cell Biol. 139:601–611 (1997)). While this activity underlies the proposed therapeutic benefit of these compounds in CF, it is possible that it may also produce toxic side effects by activating calcium-dependent processes in a wide variety of cells (Berridge, Mol. Cell. Endocrin. 98:119–24 (1994)). Since the primary affected organ in CF is the lung (Davis et al., Am. J. Respir. Crit. Care Med. 154:1229–1256 (1996); Pilewski and Frizell, Physiol. Rev. 79:Suppl: S215–S255 (1999); Rosenstein and Zeitlin, Lancet 351:277–282 (1998); Johnson et al. Nature Gen. 2:21–25 (1992)), correction of the CF defect in airway epithelial cells would dramatically reduce the morbidity associated with this disease. It is important, therefore, to determine whether therapeutically efficacious doses of thapsigargin applied directly to the lung by inhalation are clinically tolerable.

To examine this issue, six mice were exposed for 3 to 4 hours per day for 14 days to a nebulized solution of 1 $\mu$M thapsigargin in normal saline. The animals exhibited no obvious ill effects either during or between treatments. At the end of the 2 week trial, the animals were sacrificed and 4 were processed for histopathologic examination of the lungs. In all cases, the cellular architecture of the lungs (i.e., alveolar and bronchiolar architecture) was completely normal. One of the specimens exhibited a moderate peribronchiolar lymphocytic infiltration, while in the other 3 the density of peribronchiolar lymphocytes was within normal limits (data not shown).

To ensure that the dose of thapsigargin received by the mice was sufficient to rescue $\Delta$F508-CFTR in airway epithelial cells, we examined the effect of nebulized thapsigargin on $\Sigma$CFBE290$^-$ cells. These airway epithelial cells were cultured on permeable filter supports and grown with an air-liquid interface. Thus, their apical membranes are separated from the atmosphere by only a thin film of fluid, as are the apical membranes of airway epithelial cells in situ (Davis et al., Am. J. Respir. Crit. Care Med. 154:1229–1256 (1996); Pilewski and Frizell, Physiol. Rev. 79:Suppl: S215–S255 (1999)). Filter-grown $\Sigma$CFBE290$^-$ cells were exposed to 1 $\mu$M nebulized thapsigargin for 3 hours and the distribution of $\Delta$F508-CFTR was evaluated by immunofluorescence.

As can be seen in FIG. 5, treatment of cells with nebulized thapsigargin was sufficient to produce a dramatic redistribution of $\Delta$F508-CFTR to the apical plasmalemma. Since the upper airway epithelial cells in the mice must have experienced a dose of thapsigargin similar to that received by the cultured cells, it would appear that mice tolerate long-term doses of thapsigargin sufficient to produce a clinical effect without experiencing any readily detectable or significant physiologic morbidity.

Experiment 5
Secretion of $\alpha$-1 Antitrypsin from Secretion Incompetent Null Variant Affected-hepatocytes After Thapsigargin Treatment Experiment 2 is repeated using a cell line that expresses a retention mutation for $\alpha$1 antitrypsin, such as the secretion-incompetent variant, null (Hong Kong), retained in stably transfected mouse hepatoma cells (J. Biol. Chem. 269:7514–7519 (1994)). Changes in the cell phenotype are assessed by assaying cells for secretion of $\alpha$1 antitrypsin (detailed description in J. Biol. Chem. 268:2001–2008 (1993)).

Briefly, cell monolayers are pulse labeled with [$^{35}$S] methionine for 30 minutes, after which the radiolabeled media is removed and replaced with media containing an excess of unlabeled methionine. During the chase period, one set of monolayers is treated with 1 $\mu$M thapsigargin for 3 hours, while another set is incubated for 3 hours in drug free media. Secretion of $\alpha$1 antitrypsin into the media is assessed by immunoprecipitation followed by electrophoresis and autoradiography.

Results

Cells expressing the secretion-incompetent variant of $\alpha$1 antitrypsin, null (Hong Kong), are pulse labeled for 30 minutes with [$^{35}$S] methionine, after which they were incubated in non-radioactive media for 3 hours in the presence or absence of 1 $\mu$M thapsigargin. After this chase incubation, the media is collected and subjected to immunoprecipitation with anti $\alpha$1 antitrypsin antibodies. Immunoprecipitates are analyzed by SDS-PAGE followed by autoradiography.

Radiolabeled $\alpha$1 antitrypsin protein is present in the media from thapsigargin treated cells and is absent from media collected from untreated cells. These results demonstrate that thapsigargin treatment releases the mis-folded $\alpha$1 antitrypsin protein from the endoplasmic reticulum and allows it to be secreted from the cell.

Experiment 6
Toxicity Tests for Thapsigargin

Genetically uniform lab mice were given either normal drinking water (control) or drinking water which contained thapsigargin (1 $\mu$M final concentration). The non-control group of mice were given the thapsigargin-treated water over a 3 to 7 day time period. There were no deaths, illnesses or side effects noted in the mice that were given the thapsigargin water (same as control group).

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:

1. A method of treating any disease or clinical condition, wherein the method comprises administering an agent that permits the release of proteins from the endoplasmic reticulum.

2. The method of claim 1 wherein the disease or clinical condition is at least partly the result of endoplasmic reticulum-associated retention or degradation of mis-assembled or mis-folded proteins.

3. The method of claim 1 wherein the agent permits release of mis-assembled or mis-folded proteins from the endoplasmic reticulum.

4. The method of claim 1 wherein the proteins are glycoproteins.

5. The method of claim 1 wherein the disease or clinical condition is Cystic Fibrosis.

6. The method of claim 1 wherein the agent is a calcium pump inhibitor.

7. The method of claim 1 wherein the agent decreases or inhibits the functional activity of UDP glucose:glycoprotein glycosyl transferase.

8. The method of claim 1 wherein the agent decreases or inhibits activity of the endoplasmic reticulum $Ca^{++}$ ATPase.

9. The method of claim 1 wherein the agent lowers the concentration of $Ca^{++}$ in the endoplasmic reticulum.

10. The method of claim 1 wherein the agent causes release of $Ca^{++}$ from the endoplasmic reticulum.

11. The method of claim 1 wherein the agent acts as an $IP_3$ receptor agonist.

12. The method of claim 1 wherein the agent decreases or inhibits calnexin functional activity.

13. The method of claim 1 wherein the agent is thapsigargin or a derivative thereof.

14. The method of claim 1 wherein the agent is an oligonucleotide which is antisense to an mRNA that encodes a protein selected from the group consisting of UDP glucose:glycoprotein glycosyl transferase, calnexin, and $Ca^{++}$ ATPase.

15. The method of claim 1 wherein the agent is administered to the pulmonary system.

16. The method of claim 1 wherein the agent is administered as an aerosol.

17. The method of claim 1 wherein the disease is Chronic Obstructive Pulmonary Disease.

18. The method of claim 1 wherein the disease is Paroxysmal Nocturnal Hemoglobinuria.

19. The method of claim 1 wherein the disease is Familial Hypercholesterolemia.

20. The method of claim 1 wherein the disease is Tay-Sachs Disease.

21. The method of claim 1 wherein the disease is a viral disease.

22. The method of claim 1 wherein the disease is a neoplastic disease.

23. The method of claim 1 wherein the disease is Hereditary Myeloperoxidase Deficiency.

24. The method of claim 1 wherein the disease is Congenital Insulin Resistance.

25. The method of claim 1 wherein the agent is cyclopiazonic acid or a derivative thereof.

26. The method of claim 1 wherein the agent is DBHQ or a derivative thereof.

27. The method of claim 1 wherein the agent is halothane or a derivative thereof.

28. A method of treating or alleviating symptoms of a disease or clinical condition characterized by retention of proteins in the endoplasmic reticulum comprising steps of:

providing a patient suffering from the disease or clinical condition; and administering to the patient a composition comprising thapsigargin or a derivative thereof.

29. A method of treating or alleviating symptoms of a disease or clinical condition characterized by retention of proteins in the endoplasmic reticulum comprising steps of:

providing a patient suffering from the disease or clinical condition; and administering to the patient a composition comprising cyclopiazonic acid or a derivative thereof.

30. A method of treating or alleviating symptoms of a disease or clinical condition characterized by retention of proteins in the endoplasmic reticulum comprising steps of:

providing a patient suffering from the disease or clinical condition; and administering to the patient a composition comprising DBHQ or a derivative thereof.

31. A method of treating or alleviating symptoms of a disease or clinical condition characterized by retention of proteins in the endoplasmic reticulum comprising steps of:

providing a patient suffering from the disease or clinical condition; and administering to the patient a composition comprising halothane or a derivative thereof.

32. The method of any of claims 28 through 31, wherein the composition causes release of proteins from the endoplasmic reticulum.

33. The method of claim 32, wherein some or all of the proteins are misfolded or misassembled.

34. The method of any of claims 28 through 31, wherein the composition inhibits a calcium pump.

35. The method of any of claims 28 through 31, wherein the composition decreases or inhibits activity of UPD glucose:glycoprotein glycosyl transferase.

36. The method of any of claims 28 through 31, wherein the composition decreases or inhibits activity of the ER $Ca^{++}$ ATPase.

37. The method of any of claims 28 through 31, wherein the composition lowers the concentration of $Ca^{++}$ in the ER.

38. The method of any of claims 28 through 31, wherein the composition causes release of $Ca^{++}$ from the ER.

39. The method of any of claims 28 through 31, wherein the composition acts as an $IP_3$ receptor agonist.

40. The method of any of claims 28 through 31, wherein the composition decreases or inhibits calnexin activity.

41. The method of any of claims 28 through 31, wherein the disease is cystic fibrosis.

42. The method of any of claims 28 through 31, wherein the disease is selected from the group consisting of Chronic Obstructive Pulmonary Disease, Paroxysmal Nocturnal Hemoglobinuria, Familial Hypercholesterolemia, Tay-Sachs Disease, viral diseases, neoplastic diseases, Hereditary Myeloperoxidase Deficiency and Congenital Insulin Resistance.

43. The method of any of claims 28 through 31, wherein the composition is administered to the pulmonary system.

44. The method of any of claims 28 through 31, wherein the composition is administered as an aerosol.

45. A method of treating cystic fibrosis or alleviating the symptoms of cystic fibrosis, comprising the step of administering an agent that decreases or inhibits the activity of UDP glucose:glycoprotein glycosyl transferase.

46. A method of treating cystic fibrosis or alleviating the symptoms of cystic fibrosis, comprising the step of administering an agent that decreases or inhibits activity of the endoplasmic reticulum $Ca^{++}$ ATPase.

47. A method of treating cystic fibrosis or alleviating the symptoms of cystic fibrosis, comprising the step of administering an agent that lowers the concentration of $Ca^{++}$ in the endoplasmic reticulum.

48. A method of treating cystic fibrosis or alleviating the symptoms of cystic fibrosis, comprising the step of administering an agent that decreases or inhibits calnexin functional activity.

* * * * *